United States Patent
Duffy et al.

(10) Patent No.: US 7,160,870 B2
(45) Date of Patent: Jan. 9, 2007

(54) THROMBOPOIETIN MIMETICS

(75) Inventors: Kevin J. Duffy, Collegeville, PA (US); Connie Erickson-Miller, King Of Prussia, PA (US); Julian Jenkins, Collegeville, PA (US); Juan I. Luengo, Collegeville, PA (US); Sophie Visonneau, Thousand Oaks, PA (US)

(73) Assignees: SmithKline Beecham Corporation, Philadelphia, PA (US); Glaxo Group Limited, Greenford (GB)

( * ) Notice: Subject to any disclaimer, the term of this patent is extended or adjusted under 35 U.S.C. 154(b) by 198 days.

(21) Appl. No.: 10/296,688

(22) PCT Filed: May 24, 2001

(86) PCT No.: PCT/US01/16863

§ 371 (c)(1),
(2), (4) Date: Jul. 3, 2003

(87) PCT Pub. No.: WO01/89457

PCT Pub. Date: Nov. 29, 2001

(65) Prior Publication Data

US 2004/0019190 A1  Jan. 29, 2004

(51) Int. Cl.
*C07D 231/46* (2006.01)
*A61K 31/4152* (2006.01)
*A61K 31/655* (2006.01)

(52) U.S. Cl. ............... 514/150; 514/404; 534/792; 548/367.4

(58) Field of Classification Search .......... 514/150, 514/256, 312, 341, 365, 369, 381, 404; 534/753, 534/775, 792; 544/333; 546/153, 276.1, 546/268.4; 548/183, 205, 252, 364.1, 365.7, 548/367.4
See application file for complete search history.

(56) References Cited

U.S. PATENT DOCUMENTS

| | | | |
|---|---|---|---|
| 851,444 A | 4/1907 | Shulthess | |
| 2,809,963 A * | 10/1957 | Hanhart | 534/665 |
| 2,950,273 A | 8/1960 | Pelz | |
| 3,366,619 A | 1/1968 | DeLucia | |
| 4,435,417 A | 3/1984 | Toja et al. | |
| 4,510,149 A | 4/1985 | Cozzi et al. | |
| 4,686,285 A * | 8/1987 | Pedrazzi | 534/606 |
| 4,880,788 A | 11/1989 | Moake et al. | |
| 4,948,900 A | 8/1990 | Iijima et al. | |
| 5,326,776 A | 7/1994 | Winn et al. | |
| 5,482,546 A | 1/1996 | Eida et al. | |
| 5,532,202 A | 7/1996 | Yoshida | |
| 5,622,818 A | 4/1997 | Kapp et al. | |
| 5,669,967 A | 9/1997 | Hays | |
| 5,746,821 A | 5/1998 | Hays | |
| 5,760,038 A | 6/1998 | Murugesan et al. | |
| 5,932,546 A | 8/1999 | Barrett et al. | |
| 6,214,813 B1 | 4/2001 | Zhang et al. | |
| 6,238,442 B1 | 5/2001 | Schumacher et al. | |
| 6,248,871 B1 | 6/2001 | Ebenezer et al. | |
| 6,280,959 B1 | 8/2001 | Gleason et al. | |
| 6,436,915 B1 | 8/2002 | Zhang et al. | |
| 6,642,265 B1 * | 11/2003 | Luengo et al. | 514/407 |
| 6,670,387 B1 * | 12/2003 | Luengo et al. | 514/407 |
| 2003/0060453 A1 | 3/2003 | Zhang et al. | |
| 2004/0063764 A1 | 4/2004 | Takemoto et al. | |
| 2004/0082626 A1 | 4/2004 | Takemoto et al. | |
| 2005/0234020 A1 * | 10/2005 | Heerding | 514/79 |
| 2006/0069140 A1 * | 3/2006 | Miyaji et al. | 514/381 |

FOREIGN PATENT DOCUMENTS

| | | |
|---|---|---|
| DE | 193350 | 11/1904 |
| DE | 193350 | 12/1907 |
| DE | 1046220 | * 12/1958 |
| EP | 0 638 617 | 4/1994 |
| EP | 1 207 155 | 7/2000 |
| EP | 1 253 142 | 1/2001 |
| EP | 1 104 674 | 6/2001 |
| GB | 826207 | 7/1956 |
| GB | 779 880 | 7/1957 |
| JP | 2002-371213 | 12/2002 |
| WO | WO 93/17681 | 9/1993 |
| WO | WO 94/26709 | 11/1994 |
| WO | WO 96/40750 | 12/1996 |
| WO | WO 98/46606 | 10/1998 |
| WO | WO 99/15500 | 1/1999 |
| WO | WO 99/11262 | 11/1999 |
| WO | WO 00/35446 | 6/2000 |
| WO | WO 01/77080 | 1/2001 |
| WO | WO 01/07423 | 2/2001 |
| WO | WO 01/17349 | 3/2001 |
| WO | WO 01/21180 | 3/2001 |
| WO | WO 01/34585 | 5/2001 |

(Continued)

OTHER PUBLICATIONS

Minssen-Guette, et al., Bulletin De La Societe Chimique De France, 1986, No. 5, pp. 2106-2110.

(Continued)

*Primary Examiner*—Fiona T. Powers
(74) *Attorney, Agent, or Firm*—Wayne J. Dustman; Stephen Venetianer

(57) ABSTRACT

Invented are non-peptide TPO mimetics. Also invented are novel processes and intermediates used in the preparation of the presently invented compounds. Also invented is a method of treating thrombocytopenia, in a mammal, including a human, in need thereof which comprises administering to such mammal an effective amount of a selected hydroxy-1-azobenzene derivative.

22 Claims, No Drawings

FOREIGN PATENT DOCUMENTS

| WO | WO 02/059099 | 1/2002 |
|---|---|---|
| WO | WO 02/059100 | 1/2002 |
| WO | WO 02/49413 | 6/2002 |
| WO | WO 02/057300 | 7/2002 |
| WO | WO 02/085343 | 10/2002 |
| WO | WO 03/045379 | 6/2003 |
| WO | WO03/074550 | 9/2003 |
| WO | WO03/098992 | 12/2003 |
| WO | WO 03/103686 | 12/2003 |
| WO | WO 04/054515 | 7/2004 |
| WO | WO 04/096154 | 11/2004 |
| WO | WO 05/041867 | 5/2005 |

OTHER PUBLICATIONS

European Search report dated Dec. 15, 2003.
European office action dated Feb. 2, 2005.
Bussel, et al., Seminars in Hematology, 2000, vol. 37, pp. 1-49 (whole journal).
Balli, et al., Dyes, Pigm., 1981, vol. 2, No. 2, pp. 93-124.
Balli, et al., Justus Liebigs Ann. Chem., 1966, vol. 699, pp. 133-144.
Yamazaki, et al., Japn. J. Toxicol. Environ. Health, 1994, vol. 94, No. 5, pp. 448-453.
Duffin, et al., J. of the Chem. Soc., 1954, pp. 408-441.
King, et al., Scand. J. of Immunol., 1999, vol. 49, No. 2, pp. 184-192.
Konica Corp. Derwent No. 92-077508/10, 1992.
Mitsubishi Pharma Corp. Derwent Corp. Derwent No. 2003-845201/78, 2003.
Mitsubishi Pharma Corp. Derwent No. 2003-767492/72, 2003.
Balli, et al., Dyes. Pigm., 1981, vol. 2, No. 2, pp. 93-124.
Balli, et al., Justus Liebigs Ann. Chem., 1966, vol. 699, pp. 133-134.
Dziomko, et al., Chem. Heterocycl. Compd., 1984, vol. 20, No. 2, pp. 196-200.
Duffy, et al., J. Med. Chem., 2001, vol. 44, No. 22, p. 3730-3745.
Kimura, et al., FEBS Letters, 1998, vol. 428, No. 3, pp. 250-254.
Beckert, et al., Monatshefte Fur Chemie, 1989, vol. 120, pp. 1125-1137.
Lamb, et al., Nucleic Acids Research, 1995, vol. 23, No. 16, pp. 3283-3289.
Seidel, et al., Proc. Natl. Acad. Sci. USA, Mar. 1995, vol. 92, pp. 3041-3045.
Berkhout, et al., J. of Biological Chemistry, Jun. 1997, vol. 272, No. 26, pp. 16404-16413.
Vermeulen, et al., Blood, 1998, vol. 92, No. 3, pp. 894-900.
Hasegawa, et al., Int. J. Immunopharmac, 1996, vol. 18, No. 2, pp. 103-112.
Kumamoto, et al., British Journal of Haematology, 1999, vol. 105, pp. 1025-1033.
Shiotsu, et al., Experimental Hematology, 1998, vol. 26, pp. 1195-1201.
Komatsu, et al., Blood, 1996, vol. 87, No. 11, pp. 4552-4560.
Uguccioni, et al., J. Exp. Med., 1996, vol. 183, pp. 2397-2384.
Taylor, et al., J. Org. Chem., 1987, vol. 52, pp. 4107-4110.
Kuter, et al., Seminars in Hematology, Apr. 2000, vol. 37, No. 2, pp. 41-49.
Ballestrero, et al., Oncology, 2000, vol. 59, pp. 7-13.
Sawai, et al., Journal of Leukocyte Biology, Jul. 2000, vol. 68, pp. 137-143.
Vigon, et al., Proc. Natl. Acad. Sci. USA, Jun. 1992, vol. 89, pp. 5640-5644.
Laurenz, et al., Comp. Biochem Physiol., 1997, vol. 116A, No. 4, pp. 369-377.
Metcalf, et al., Nature, Jun. 16, 1994, vol. 369, pp. 519-520.
Bussel, et al., Seminars in Hematology, 2000, vol. 37, pp. 1-49 (Table of Contents).
McDonald, et al., Am. J. of Pediatric Hematology/Oncology, 1992, vol. 14, No. 1, pp. 8-21.
Souyri, et al., Cell, 1990, vol. 63, pp. 1137-1147.
Bazan, et al., Pro. Natl. Acad. Sci. USA, Sep. 1990, vol. 87, pp. 6934-6938.
Sauvage, et al., Nature, Jun. 16, 1994, vol. 369, pp. 533-538.
Wendling, et al., Nature, Jun. 16, 1994, vol. 369, pp. 571-574.
Kaushansky, et al., Nature, Jun. 16, 1994, vol. 369, pp. 568-571.
Bartley, et al., Cell, 1994, vol. 77, pp. 1117-1124.
King, et al., The Journal of Immunology, 2000, pp. 3774-3782.
Kikuta, et al., Experimental Hematology, 2000, vol. 28, pp. 311-317.
Somlo, et al., Blood, May 1, 1992, vol. 93, No. 9, pp. 2798-2806.
Kirley-Neumann, et al., Cytokines, Cellular & Molecular Therapy, 2000, vol. 6, pp. 47-56.
Egger, et al., Bone Marrow Transplant, 1998, vol. 22, pp. 34-35.
Gaudron, et al., Stem Cells, 1999, vol. 17, pp. 100-106.
Fetscher, et al., Current Opinion in Hematology, 2000, vol. 7, pp. 255-260.
Clemons, et al., Breast Cancer Res. Treatment, 1999, vol. 57, pp. 127.
Greene, "Protective Groups in Organic Synthesis", 1981, Table of Contents.
Methia, et al., Blood, 1993, vol. 82, No. 5, pp. 1395-1401.
A. Esteve, Ann. Pharm. Franc., 1950, vol. 8, No. 9-10.
PCT/US2004/13468 filed Apr. 29, 2004.
PCT/US2004/034944 filed Oct. 21, 2004.
Olszewski, et al., J. Org. Chem., 1994, vol. 59, pp. 4285-4296.
Yamazaki, et al., Database HCAPLUS, AN 1995: Abstract, 196968.
A. Esteve, Ann. Pharm. Franc., 1950, vol. 8, No. 9-10, pp. 594-604.
Morris, et al., Anti-Cancer Drugs, 1997, vol. 8, No. 8, pp. 746-755.
Duffy, et al., J. Med. Chem., 2001, vol. 44, No. 22, Abstract No. XP002197261.
Olszewski, et al., Database CAPLUS on STN, 1995, Chem. Abstracts, No. 122:81695.

* cited by examiner

THROMBOPOIETIN MIMETICS

FIELD OF THE INVENTION

This invention relates to thrombopoietin (TPO) mimetics and their use as promoters of thrombopoiesis and megakaryocytopoiesis.

BACKGROUND OF THE INVENTION

Megakaryocytes are bone marrow-derived cells, which are responsible for producing circulating blood platelets. Although comprising <0.25% of the bone marrow cells in most species, they have >10 times the volume of typical marrow cells. See Kuter et al. *Proc. Natl. Acad. Aci. USA* 91: 11104–11108 (1994). Megakaryocytes undergo a process known as endomitosis whereby they replicate their nuclei but fail to undergo cell division and thereby give rise to polypoid cells. In response to a decreased platelet count, the endomitotic rate increases, higher ploidy megakaryocytes are formed, and the number of megakaryocytes may increase up to 3-fold. See Harker *J. Clin. Invest.* 47: 458–465 (1968). In contrast, in response to an elevated platelet count, the endomitotic rate decreases, lower ploidy megakaryocytes are formed, and the number of megakaryocytes may decrease by 50%.

The exact physiological feedback mechanism by which the mass of circulating platelets regulates the endomitrotic rate and number of bone marrow megakaryocytes is not known. The circulating thrombopoietic factor involved in mediating this feedback loop is now thought to be thrombopoietin (TPO). More specifically, TPO has been shown to be the main humoral regulator in situations involving thrombocytopenia. See, e.g., Metcalf Nature 369:519–520 (1994). TPO has been shown in several studies to increase platelet counts, increase platelet size, and increase isotope incorporation into platelets of recipient animals. Specifically, TPO is thought to affect megaklaryocytopoiesis in several ways: (1) it produces increases in megakaryocyte size and number; (2) it produces an increase in DNA content, in the form of polyploidy, in megakaryocytes; (3) it increases megakaryocyte endomitosis; (4) it produces increased maturation of megakaryocytes; and (5) it produces an increase in the percentage of precursor cells, in the form of small acetylcholinesterase-positive cells, in the bone marrow.

Because platelets (thrombocytes) are necessary for blood clotting and when their numbers are very low a patient is at risk of death from catastrophic hemorrhage, TPO has potential useful application in both the diagnosis and the treatment of various hematological disorders, for example, diseases primarily due to platelet defects (see Harker et al. *Blood* 91: 4427–4433 (1998)). Ongoing clinical trials with TPO have indicated that TPO can be administered safely to patients (see Basser et al. Blood 89: 3118–3128 (1997); Fanucchi et al. *New Engl. J. Med.* 336: 404–409 (1997)). In addition, recent studies have provided a basis for the projection of efficacy of TPO therapy in the treatment of thrombocytopenia, and particularly thrombocytopenia resulting from chemotherapy, radiation therapy, or bone marrow transplantation as treatment for cancer or lymphoma. (See Harker, *Curr. Onin. Hematol.* 6: 127–134 (1999)).

The gene encoding TPO has been cloned and characterized. See Kuter et al., *Proc. Natl. Acad. Sci. USA* 91: 11104–11124 (1994); Barley et al., *Cell* 77: 1117–1124 (1994); Kaushansky et al., *Nature* 369:568–571 (1994); Wendling et al., *Nature* 369: 571–574 (1994); and Sauvage et al., *Nature* 369: 533–538 (1994). Thrombopoietin is a glycoprotein with at least two forms, with apparent molecular masses of 25 kDa and 31 kDa, with a common N-terminal amino acid; sequence. See, Baatout, *Haemostasis* 27: 1–8 (1997); Kaushansky, *New Engl. J. Med.* 339: 746–754 (1998). Thrombopoietin appears to have two distinct regions separated by a potential Arg-Arg cleavage site. The amino-terminal region is highly conserved in man and mouse, and has some homology with erythropoietin and interferon-a and interferon-b. The carboxy-terminal region shows wide species divergence.

The DNA sequences and encoded peptide sequences for human TPO receptor (TPO-R; also known as c-mpl) have been described. (See, Vigon et al. *Proc. Natl. Acad. Sci. USA* 89: 5640–5644 (1992)). TPO-R is a member of the haematopoietin growth factor receptor family, a family characterized by a common structural design of the extracellular domain, including for conserved C residues in the N-terminal portion and a WSXWS motif close to the transmembrane region. (See Bazan *Proc. Natl. Acad. Sci. USA* 87: 6934–6938 (1990)). Evidence that this receptor plays a functional role in hematopoiesis includes observations that its expression if restricted to spleen, bone marrow, or fetal liver in mice (see Souyri et al. *Cell* 63: 1137–1147 (1990)) and to megakaryocytes, platelets, and $CD34^+$ cells in humans (see Methia et al. *Blood* 82: 1395–1401 (1993)). Further evidence for TPO-R as a key regulator of megakaryopoiesis is the fact that exposure of $CD34^+$ cells to synthetic oligonucleotides antisense to TPO-R RNA significantly inhibits the appearance of megakaryocyte colonies without affecting erythroid or myeloid colony formation. Some workers postulate that the receptor functions as a homodimer, similar to the situation with the receptors for G-CSF and erythropoietin. (see Alexander et al. *EMBO J.* 14: 5569–5578 (1995)).

The slow recovery of platelet levels in patients suffering from thrombocytopenia is a serious problem, and has lent urgency to the search for a blood growth factor agonist able to accelerate platelet regeneration (see Kuter, *Seminars in Hematology*, 37: Supp 4: 41–49 (2000)).

It would be desirable to provide compounds which allow for the treatment of thrombocytopenia by acting as a TPO mimetic.

As disclosed herein it has unexpectedly been discovered that certain hydroxy-1-azo-benzene derivatives are effective as agonists of the TPO receptor, they are potent TPO mimetics.

SUMMARY OF THE INVENTION

This invention relates to compounds of Formula (I):

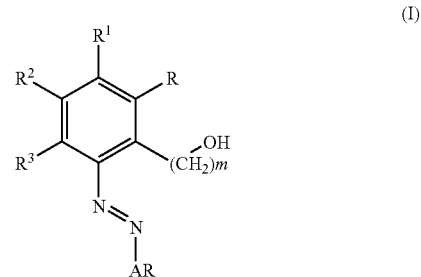

wherein:
R, $R^1$, $R^2$ and $R^3$ are each independently selected from hydrogen, $C_{1-6}$alkyl, $—(CH_2)_pOR^4$, $—C(O)OR^4$, formyl, nitro, cyano, halogen, aryl, substituted aryl, substituted alkyl, —S(O)$_n$R$^4$, cycloalkyl, —NR$^5$R$^6$, protected —OH, —CONR$^5$R$^6$, phosphonic acid, sulfonic acid, phosphinic acid, —SO$_2$NR$^5$R$^6$, and a heterocyclic methylene substituent as represented by Formula (III),

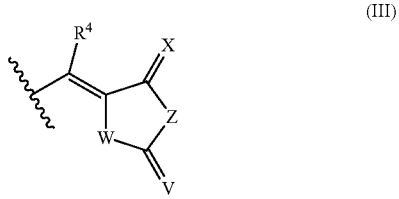

(III)

where,
p is 0–6,
n is 0–2,
V, W, X and Z are each independently selected from O, S and NR$^{16}$, where R$^{16}$ is selected from: hydrogen, alkyl, cycloalkyl, C$_1$–C$_{12}$aryl, substituted alkyl, substituted cycloalkyl and substituted C$_1$–C$_{12}$aryl,
R$^4$ is selected from: hydrogen, alkyl, cycloalkyl, C$_1$–C$_{12}$aryl, substituted alkyl, substituted cycloalkyl and substituted C$_1$–C$_{12}$aryl, and
R$^5$ and R$^6$ are each independently selected from hydrogen, alkyl, substituted alkyl, C$_{3-6}$cycloalkyl, and aryl,
or R$^5$ and R$^6$ taken together with the nitrogen to which they are attached represent a 5 to 6 member saturated ring containing up to one other heteroatom selected from oxygen and nitrogen;
m is 0–6; and
AR is a cyclic or polycyclic aromatic ring containing from 3 to 16 carbon atoms and optionally containing one or more heteroatoms, provided that when the number of carbon atoms is 3 the aromatic ring contains at least two heteroatoms and when the number of carbon atoms is 4 the aromatic ring contains at least one heteroatom, and optionally substituted with one or more substituents selected from the group consisting of: alkyl, substituted alkyl, aryl, substituted cycloalkyl, substituted aryl, aryloxy, oxo, hydroxy, alkoxy, cycloalkyl, acyloxy, amino, N-acylamino, nitro, cyano, halogen, —C(O)OR$^4$, —C(O)NR$^{10}$R$^{11}$, —S(O)$_2$NR$^{10}$R$^{11}$, —S(O)$^n$R$^4$ and protected —OH,
where n is 0–2,
R$^4$ is hydrogen, alkyl, cycloalkyl, C$_1$–C$_{12}$aryl, substituted alkyl, substituted cycloalkyl and substituted C$_1$–C$_{12}$aryl, and
R$^{10}$ and R$^{11}$ are independently hydrogen, cycloalkyl, C$_1$–C$_{12}$aryl, substituted cycloalkyl, substituted C$_1$–C$_{12}$aryl, alkyl or alkyl substituted with one or more substituents selected from the group consisting of: alkoxy, acyloxy, aryloxy, amino, N-acylamino, oxo, hydroxy, —C(O)OR$^4$, —S(O)$_n$R$^4$, —C(O)NR$^4$R$^4$, —S(O)$_2$NR$^4$R$^4$, nitro, cyano, cycloalkyl, substituted cycloalkyl, halogen, aryl, substituted aryl and protected —OH,
or R$^{10}$ and R$^{11}$ taken together with the nitrogen to which they are attached represent a 5 to 6 member saturated ring containing up to one other heteroatom selected from oxygen and nitrogen,
where R$^4$ is as described above and n is 0–2;
and pharmaceutically acceptable salts, hydrates, solvates and esters thereof;

provided that at least one of R, R$^1$, R$^2$ and R$^3$ is a substituted aryl group or a heterocyclic methylene substituent as represented in Formula (III).

This invention relates to a method of treating thrombocytopenia, which comprises administering to a subject in need thereof an effective amount of a TPO mimetic compound of Formula (I).

The present invention also relates to the discovery that the compounds of Formula (I) are active as agonists of the TPO receptor.

In a further aspect of the invention there is provided novel processes and novel intermediates useful in preparing the presently invented TPO mimetic compounds.

Included in the present invention are pharmaceutical compositions comprising a pharmaceutical carrier and compounds useful in the methods of the invention.

Also included in the present invention are methods of co-administering the presently invented TPO mimetic compounds with further active ingredients.

DETAILED DESCRIPTION OF THE INVENTION

This invention relates to compounds of Formula (I) as described above.

Included among the presently invented compounds of Formula (I) are those having Formula (V):

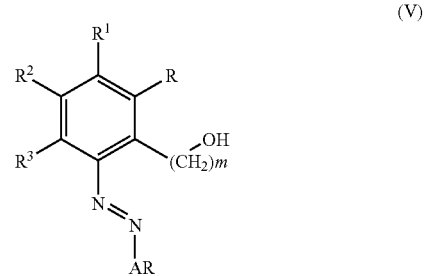

(V)

wherein:
R, R$^1$, R$^2$ and R$^3$ are each independently selected from hydrogen, C$_{1-6}$alkyl, C$_{1-6}$alkoxy, —(CH$_2$)$_p$OR$^4$, —C(O)OR$^4$, formyl, nitro, cyano, halogen, aryl, substituted aryl, substituted alkyl, —S(O)$_n$R$^4$, cycloalkyl, —NR$^5$R$^6$, protected —OH, —CONR$^5$R$^6$, phosphonic acid, sulfonic acid, phosphinic acid and —SO$_2$NR$^5$R$^6$,
where,
p is 0–6,
n is 0–2,
R$^4$ is selected from: hydrogen, alkyl, cycloalkyl, C$_1$–C$_{12}$aryl, substituted alkyl, substituted cycloalkyl and substituted C$_1$–C$_{12}$aryl, and
R$^5$ and R$^6$ are each independently selected from hydrogen, alkyl, substituted alkyl, C$_{3-6}$cycloalkyl, and aryl,
or R$^5$ and R$^6$ taken together with the nitrogen to which they are attached represent a 5 to 6 member saturated ring containing up to one other heteroatom selected from oxygen and nitrogen;
m is 0–6; and
AR is a cyclic or polycyclic aromatic ring containing from 3 to 16 carbon atoms and optionally containing one or more heteroatoms, provided that when the number of carbon atoms is 3 the aromatic ring contains at least two heteroatoms and when the number of carbon atoms is 4 the aromatic ring contains at least one heteroatom, and optionally substituted with one or more substituents selected from the group consisting of: alkyl, substituted alkyl, aryl, substituted cycloalkyl, substituted aryl, aryloxy, oxo, hydroxy, alkoxy, cycloalkyl, acyloxy, amino, N-acylamino, nitro, cyano, halogen, —C(O)OR$^4$, —C(O)NR$^{10}$R$^{11}$, —S(O)$_2$NR$^{10}$R$^{11}$, —S(O)$^n$R$^4$ and protected —OH, where n is 0–2, R$^4$ is hydrogen, alkyl, cycloalkyl, C$_1$–C$_{12}$aryl, substituted alkyl, substituted cycloalkyl and substituted C$_1$–C$_{12}$aryl; and R$^{10}$ and R$^{11}$ are independently hydrogen, cycloalkyl, C$_1$–C$_{12}$aryl, substituted cycloalkyl, substituted C$_1$–C$_{12}$aryl, alkyl or alkyl substituted with one or more substituents selected from the group consisting of: alkoxy, acyloxy, aryloxy, amino, N-acylamino, oxo, hydroxy, —C(O)OR$^4$, —S(O)$_n$R$^4$, —C(O)NR$^4$R$^4$, —S(O)$_2$NR$^4$R$^4$, nitro, cyano, cycloalkyl, substituted cycloalkyl, halogen, aryl, substituted aryl and protected —OH, or R$^{10}$ and R$^{11}$ taken together with the nitrogen to which they are attached represent a 5 to 6 member saturated ring containing up to one other heteroatom selected from oxygen and nitrogen, where R$^4$ is as described above and n is 0–2;

and pharmaceutically acceptable salts, hydrates, solvates and esters thereof;

provided that at least one of R, R$^1$, R$^2$ and R$^3$ is a substituted aryl group.

Preferred among the presently invented compounds of Formula (I) are those having Formula (II):

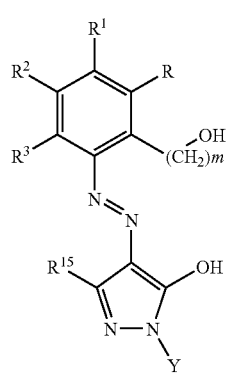

(II)

wherein:

R, R$^1$, R$^2$ and R$^3$ are each independently selected from hydrogen, C$_{1-6}$alkyl, —(CH$_2$)$_p$OR$^4$, —C(O)OR$^4$, formyl, nitro, cyano, halogen, aryl, substituted aryl, substituted alkyl, —S(O)$_n$R$^4$, cycloalkyl, —NR$^5$R$^6$, protected —OH, —CONR$^5$R$^6$, phosphonic acid, sulfonic acid, phosphinic acid, —SO$_2$NR$^5$R$^6$, and a heterocyclic methylene substituent as represented by Formula (III),

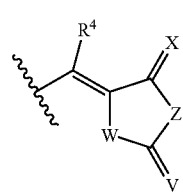

(III)

where p is 0–6, n is 0–2,

V, W, X and Z are each independently selected from O, S, and NR$^{16}$, where R$^{16}$ is selected from: hydrogen, alkyl, cycloalkyl, C$_1$–C$_{12}$aryl, substituted alkyl, substituted cycloalkyl and substituted C$_1$–C$_{12}$aryl, R$^4$ is hydrogen, alkyl, cycloalkyl, C$_1$–C$_{12}$aryl, substituted alkyl, substituted cycloalkyl and substituted C$_1$–C$_{12}$aryl, and R$^5$ and R$^6$ are each independently selected from hydrogen, alkyl, substituted alkyl, C$_{3-6}$cycloalkyl, and aryl, or R$^5$ and R$^6$ taken together with the nitrogen to which they are attached represent a 5 to 6 member saturated ring containing up to one other heteroatom selected from oxygen and nitrogen;

R$^{15}$ is selected from the group consisting of alkyl, C$_1$–C$_{12}$aryl, hydroxy, alkoxy, substituted alkyl, substituted C$_1$–C$_{12}$aryl and halogen;

m is 0–6; and

Y is selected from alkyl, substituted alkyl and a cyclic or polycyclic aromatic ring containing from 3 to 14 carbon atoms and optionally containing from one to three heteroatoms, provided that when the number of carbon atoms is 3 the aromatic ring contains at least two heteroatoms and when the number of carbon atoms is 4 the aromatic ring contains at least one heteroatom, and optionally substituted with one or more substituents selected from the group consisting of: alkyl, substituted alkyl, C$_1$–C$_{12}$aryl, substituted cycloalkyl, substituted C$_1$–C$_{12}$aryl, hydroxy, aryloxy, alkoxy, cycloalkyl, nitro, cyano, halogen and protected —OH;

and pharmaceutically acceptable salts, hydrates, solvates and esters thereof;

provided that at least one of R, R$^1$, R$^2$ and R$^3$ is a substituted aryl group or a heterocyclic methylene substituent as represented in Formula (III).

Included among the presently invented compounds of Formula (II) are compounds in which R$^{15}$ is not alkoxy.

Included among the presently invented compounds of Formula (II) are those having Formula (VI):

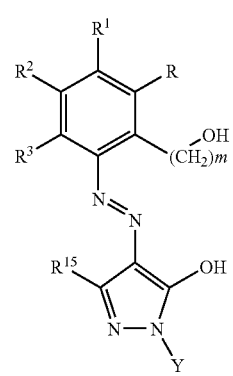

(VI)

wherein:

R, R$^1$, R$^2$ and R$^3$ are each independently selected from hydrogen, C$_{1-6}$alkyl, C$_{1-6}$alkoxy, —(CH$_2$)$_p$OR$^4$, —C(O)OR$^4$, formyl, nitro, cyano, halogen, aryl, substituted aryl, substituted alkyl, —S(O)$_n$R$^4$, cycloalkyl, —NR$^5$R$^6$, protected —OH, —CONR$^5$R$^6$, phosphonic acid, sulfonic acid, phosphinic acid and —SO$_2$NR$^5$R$^6$, where p is 0–6, n is 0–2, R$^4$ is hydrogen, alkyl, cycloalkyl, C$_1$–C$_{12}$aryl, substituted alkyl, substituted cycloalkyl and substituted C$_1$–C$_{12}$aryl, and R$^5$ and R$^6$ are each independently selected from hydrogen, alkyl, substituted alkyl, C$_{3-6}$cycloalkyl, and aryl, or R$^5$ and R$^6$ taken together with the nitrogen to which they are attached represent a 5 to 6 member saturated ring containing up to one other heteroatom selected from oxygen and nitrogen;

R$^{15}$ is selected from the group consisting of alkyl, C$_1$–C$_{12}$aryl, hydroxy, alkoxy, substituted alkyl, substituted C$_1$–C$_{12}$aryl and halogen;

m is 0–6; and

Y is selected from alkyl, substituted alkyl and a cyclic or polycyclic aromatic ring containing from 3 to 14 carbon atoms and optionally containing from one to three heteroatoms, provided that when the number of carbon atoms is 3 the aromatic ring contains at least two heteroatoms and when the number of carbon atoms is 4 the aromatic ring contains at least one heteroatom, and optionally substituted with one or more substituents selected from the group consisting of: alkyl, substituted alkyl, C$_1$–C$_{12}$aryl, substituted cycloalkyl, substituted C$_1$–C$_{12}$aryl, hydroxy, aryloxy, alkoxy, cycloalkyl, nitro, cyano, halogen and protected —OH;

and pharmaceutically acceptable salts, hydrates, solvates and esters thereof;

provided that at least one of R, R$^1$, R$^2$ and R$^3$ is a substituted aryl group.

Also included among the presently invented compounds of Formula (II) are compounds of Formula (VI) in which R$^{15}$ is not alkoxy.

Preferred among the presently invented Formula VI compounds are those in which, either:

R is a substituted aryl; and R$^1$ is hydrogen;

or:

R is hydrogen; and R$^1$ is a substituted aryl;

and in either case:

R$^2$ and R$^3$ are each independently selected from hydrogen, C$_{1-6}$alkyl, C$_{1-6}$alkoxy, nitro, cyano, halogen, aryl, substituted aryl, substituted alkyl, cycloalkyl, phosphonic acid, phosphinic acid and sulfonic acid;

R$^{15}$ is selected from the group consisting of alkyl, substituted alkyl, C$_1$–C$_{12}$aryl, alkoxy and halogen;

m is 0–4; and

Y is selected from, phenyl, pyridinyl and pyrimidinyl, where the phenyl, pyridinyl and pyrimidinyl are optionally substituted with from one to three substituents selected from the group consisting of: alkyl, substituted alkyl, C$_1$–C$_{12}$aryl, substituted C$_1$–C$_{12}$aryl, alkoxy and halogen;

and pharmaceutically acceptable salts, hydrates, solvates and esters thereof.

Particularly preferred among the presently invented Formula VI compounds are those in which, R is a substituted C$_1$–C$_{12}$aryl; and R$^1$ is hydrogen;

R$^2$ and R$^3$ are each independently selected from hydrogen, C$_{1-6}$alkyl, C$_{1-6}$alkoxy, nitro, cyano, halogen, substituted alkyl and cycloalkyl;

R$^{15}$ is selected from the group consisting of alkyl, substituted alkyl, C$_1$–C$_{12}$aryl, alkoxy and halogen;

m is 0–2; and

Y is selected from, phenyl, pyridinyl and pyrimidinyl, where the phenyl, pyridinyl and pyrimidinyl are optionally substituted with from one to three substituents selected from the group consisting of: alkyl, substituted alkyl, C$_1$–C$_{12}$aryl, substituted C$_1$–C$_{12}$aryl, alkoxy and halogen;

and pharmaceutically acceptable salts, hydrates, solvates and esters thereof.

The most preferred among the presently invented Formula VI compounds are those in which, R is a substituted phenyl or pyridinyl ring; and R$^1$ is hydrogen;

R$^2$ and R$^3$ are each independently selected from hydrogen, C$_{1-6}$alkyl, substituted alkyl and halogen;

R$^{15}$ is selected from the group consisting of C$_{1-4}$alkyl, C$_{1-4}$alkoxy, C$_1$–C$_{12}$aryl and halogen;

m is 0; and

Y is selected from, phenyl, pyridinyl and pyrimidinyl, where the phenyl, pyridinyl and pyrimidinyl is optionally substituted with from one to three substituents selected from the group consisting of: alkyl, substituted alkyl, C$_1$–C$_{12}$aryl, substituted C$_1$–C$_{12}$aryl, alkoxy and halogen;

and pharmaceutically acceptable salts, hydrates, solvates and esters thereof.

Preferred among the presently invented compounds are:

4'-{N'-[1-(3,4-Dimethylphenyl)-3-methyl-5-oxo-1,5-dihydropyrazol-4-ylidene]hydrazino}-3'-hydroxybiphenyl-4-carboxylic acid;

4'-{N'-[1-(3,4-Dimethylphenyl)-3-methyl-5-oxo-1,5-dihydropyrazol-4-ylidene]hydrazino}-3'-hydroxybiphenyl-3-carboxylic acid;

3'-{N'-[1-(3,4-Dimethylphenyl)-3-methyl-5-oxo-1,5-dihydropyrazol-4-ylidene]hydrazino}-2'-hydroxybiphenyl-3-carboxylic acid;

3'-{N'-[1-(4-tert-Buthylphenyl)-3-methyl-5-oxo-1,5-dihydropyrazol-4-ylidene]hydrazino}-2'-hydroxybiphenyl-3-carboxylic acid;

2-Aza-3'-{N'-[1-(4-tert-butylphenyl)-3-methyl-5-oxo-1,5-dihydropyrazol-4-ylidene]hydrazino}-5'-chloro-2'-hydroxybiphenyl-3-carboxylic acid;

2-Aza-3'-{N'-[1-(4-tert-butylphenyl)-3-methyl-5-oxo-1,5-dihydropyrazol-4-ylidene]hydrazino}-2'-hydroxybiphenyl-3-carboxylic acid;

3-Aza-3'-{N'-[1-(4-tert-butylphenyl)-3-methyl-5-oxo-1,5-dihydropyrazol-4-ylidene]hydrazino}-2'-hydroxybiphenyl-5-carboxylic acid;

2-Aza-5'-chloro-3'-{N'-[1-(3,4-dimethylphenyl)-3-methyl-5-oxo-1,5-dihydropyrazol-4-ylidene]hydrazino}-2'-hydroxybiphenyl-3-carboxylic acid;

2-Aza-3'-{N'-[1-(4-tert-butylphenyl)-3-methyl-5-oxo-1,5-dihydropyrazol-4-ylidene]hydrazino}-2'-hydroxy-5'-methylbiphenyl-3-carboxylic acid;

2-Aza-3'-{N'-[1-(3,4-dimethylphenyl)-3-methyl-5-oxo-1,5-dihydropyrazol-4-ylidene]hydrazino}-2'-hydroxy-5'-methylbiphenyl-3-carboxylic acid;

3'-{N'-[1-(4-tert-Buthylphenyl)-3-methyl-5-oxo-1,5-dihydropyrazol-4-ylidene]hydrazino}-2'-hydroxy-5'-methylbiphenyl-3-carboxylic acid;

3-{N'-[1-(3,4-dimethylphenyl)-3-methyl-5-oxo-1,5-dihydropyrazol-4-ylidene]hydrazino}-2-hydroxy-3'-tetrazol-5-ylbiphenyl;

3'-{N'-[1-(3,4-dimethylphenyl)-3-methyl-5-oxo-1,5-dihydropyrazol-4-ylidene]hydrazino}-5'-fluoro-2'-hydroxybiphenyl-3-carboxylic acid;

7-({N'-[1-(3,4-dimethylphenyl)-3-methyl-5-oxo-1,5-dihydropyrazol-4-ylidene]hydrazino}-2-hydroxyphenyl)quinolin-4[1H]-one-3-carboxylic acid;

7-({N'-[1-(4-tert-butylphenyl)-3-methyl-5-oxo-1,5-dihydropyrazol-4-ylidene]hydrazino}-2-hydroxyphenyl)quinolin-4[1H]-one-3-carboxylic acid;

3-Aza-3'-{N'-[1-(3,4-dimethylphenyl)-3-methyl-5-oxo-1,5-dihydropyrazol-4-ylidene]hydrazino}-2'-hydroxybiphenyl-5-carboxylic acid;

3-Aza-3'-(N'-[1-{3-methyl-[4-(1-methylethyl)phenyl]]-5-oxo-1,5-dihydropyrazol-4-ylidene}hydrazino)-2'-hydroxybiphenyl-5-carboxylic acid;

3-Aza-3'-{N'-[1-(4-tertbutylphenyl-3-methyl-5-oxo-1,5-dihydropyrazol-4-ylidene]hydrazino}-2'-hydroxybiphenyl-5-carboxylic acid;

5'-Chloro-3'-{N'-[1-(3,4-dimethylphenyl)-3-methyl-5-oxo-1,5-dihydropyrazol-4-ylidene]hydrazino}-2'-hydroxybiphenyl-3-carboxylic acid;

3'-{N'-[1-(3,4-Dimethylphenyl)-3,5-dioxo-1,5-dihydropyrazol-4-ylidene]hydrazino}-2'-hydroxybiphenyl-3-carboxylic acid;

3'-{N'-[1-(2-Ethoxy-2-oxoethyl)-3-methyl-5-oxo-1,5-dihydropyrazol-4-ylidene]hydrazino}-2'-hydroxybiphenyl-3-carboxylic acid;

3'-{N'-[1-(3,4-dimethylphenyl)-3-methyl-5-oxo-1,5-dihydropyrazol-4-ylidene]hydrazino}-2-hydroxy-4'-(tetrazol-5-yl)biphenyl;

3'-{N'-{1-[2-(N-tert-butyl)amino-2-oxoethyl]-3-methyl-5-oxo-1,5-dihydropyrazol-4-ylidene}hydrazino}-2'-hydroxybiphenyl-3-carboxylic acid;

3'-{N'-[3-Chloro-1-(3,4-dimethylphenyl)-5-oxo-1,5-dihydropyrazol-4-ylidene]hydrazino}-2'-hydroxybiphenyl-3-carboxylic acid;

5-chloro-3-{N'-[1-(3,4-dimethylphenyl)-3-methyl-5-oxo-1,5-dihydropyrazol-4-ylidene]hydrazino}-2-hydroxy-4'-(tetrazol-5-yl)biphenyl;

3'-{N'-[1-(3,4-Dimethylphenyl)-3-methyl-5-oxo-1,5-dihydropyrazol-4-ylidene]hydrazino}-2'-hydroxybiphenyl-3,5-dicarboxylic acid;

3-Aza-3'-{N'-[1-(3,4-dimethylphenyl)-3-methyl-5-oxo-1,5-dihydropyrazol-4-ylidene]hydrazino}-2'-hydroxy-5'-methylbiphenyl-5-carboxylic acid;

3'-{N'-[1-(3,4-Dimethylphenyl)-3-methyl-5-oxo-1,5-dihydropyrazol-4-ylidene]hydrazino}-2'-hydroxybiphenyl-4-carboxylic acid;

3'-{N'-[1-(3,4-Dimethylphenyl)-3-methoxy-5-oxo-1,5-dihydropyrazol-4-ylidene]hydrazino}-2'-hydroxybiphenyl-3-carboxylic acid;

3'-{N'-[1-(4-methoxyphenyl)-3-methyl-5-oxo-1,5-dihydropyrazol-4-ylidene]hydrazino}-2-hydroxybiphenyl-3-carboxylic acid;

(3-{N'-[1-(3,4-dimethylphenyl)-3-methyl-5-oxo-1,5-dihydropyrazol-4-ylidene]hydrazino}-2-hydroxy-3'-biphenyl)-1,1,1,-trifluoromethanesulfonamide;

3'-{N'-[1-(3,4-Dichlorophenyl)-3-methyl-5-oxo-1,5-dihydropyrazol-4-ylidene]hydrazino}-2'-hydroxybiphenyl-3-carboxylic acid;

3'-{N'-[3-methyl-5-oxo-1-(3-trifluoromethylphenyl)-1,5-dihydropyrazol-4-ylidene]hydrazino}-2'-hydroxybiphenyl-3-carboxylic acid;

8-{N'-[1-(3,4-dimethylphenyl)-3-methyl-5-oxo-1,5-dihydropyrazol-4-ylidene]hydrazino}-quinolin-4[1H]-one-3-carboxylic acid;

3'-{N'-[3-methyl-5-oxo-1-(4-trifluoromethylphenyl)-1,5-dihydropyrazol-4-ylidene]hydrazino}-2'-hydroxybiphenyl-3-carboxylic acid;

3'-{N'-[3-methyl-5-oxo-1-(4-N-methylcarboxamidolphenyl)-1,5-dihydropyrazol-4-ylidene]hydrazino}-2'-hydroxybiphenyl-3-carboxylic acid;

N-[1-(3'-{N'-[1-(3,4-dimethylphenyl)-3-methyl-5-oxo-1,5-dihydropyrazol-4-ylidene]hydrazino}-2'-hydroxybiphenyl-3-yl)methanoyl]methanesulfonamide;

3'-{N'-[3-methyl-5-oxo-1-phenyl-1,5-dihydropyrazol-4-ylidene]hydrazino}-2'-hydroxybiphenyl-3-carboxylic acid;

3'-{N'-[3-methyl-1-(4-methylphenyl)-5-oxo-1,5-dihydropyrazol-4-ylidene]hydrazino}-2'-hydroxybiphenyl-3-carboxylic acid;

3'-{N'-[1-(4-chlorophenyl)-3-methyl-5-oxo-1,5-dihydropyrazol-4-ylidene]hydrazino}-2'-hydroxybiphenyl-3-carboxyic acid;

3'-{N'-[1-(4-fluorophenyl)-3-methyl-5-oxo-1,5-dihydropyrazol-4-ylidene]hydrazino}-2'-hydroxybiphenyl-3-carboxylic acid;

3'-{N'-[3-methyl-5-oxo-1-(4-trifluoromethoxyphenyl)-1,5-dihydropyrazol-4-ylidene]hydrazino}-2'-hydroxybiphenyl-3-carboxylic acid;

3'-{N'-[1-(3,4-dimethylphenyl)-3-ethoxy-5-oxo-1,5-dihydropyrazol-4-ylidene]hydrazino}-2'-hydroxybiphenyl-3-carboxylic acid;

3'-{N'-[1-(3,4-dimethylphenyl)-3-(1-methylethoxy)-5-oxo-1,5-dihydropyrazol-4-ylidene]hydrazino}-2'-hydroxybiphenyl-3-carboxylic acid;

3'-{N'-[3-tert-butyl-1-(3,4-dimethylphenyl)-5-oxo-1,5-dihydropyrazol-4-ylidene]hydrazino}-2'-hydroxybiphenyl-3-carboxylic acid;

3'-{N'-[3-methyl-1-(4-methyl-2,3,5,6-tetrafluorophenyl)-5-oxo-1,5-dihydropyrazol-4-ylidene]hydrazino}-2'-hydroxybiphenyl-3-carboxylic acid;

3'-{N'-[1-(4-fluoro-3-methylphenyl)-3-methyl-5-oxo-1,5-dihydropyrazol-4-ylidene]hydrazino}-2'-hydroxybiphenyl-3-carboxylic acid;

3'-{N'-[1-(3,4-dimethylphenyl)-3-phenyl-5-oxo-1,5-dihydropyrazol-4-ylidene]hydrazino}-2'-hydroxybiphenyl-3-carboxylic acid;

3-{N'-[1-(3,4-dimethylphenyl)-5-oxo-3-phenyl-1,5-dihydropyrazol-4-ylidene]hydrazino}-2-hydroxy-3'-tetrazol-5-ylbiphenyl;

3-{N'-[1-(3,4-dimethylphenyl)-3-methoxy-5-oxo-1,5-dihydropyrazol-4-ylidene]hydrazino}-2-hydroxy-3'-tetrazol-5-ylbiphenyl;

3-{N'-[1-(3,4-dimethylphenyl)-3-etboxy-5-oxo-1,5-dihydropyrazol-4-ylidene]hydrazino}-2-hydroxy-3'-tetrazol-5-ylbiphenyl;

3-{N'-[1-(3,4-dimethylphenyl)-3-(1-methylethoxy)-5-oxo-1,5-dihydropyrazol-4-ylidene]hydrazino}-2-hydroxy-3'-tetrazol-5-ylbiphenyl;

3-{N'-[1-(4-fluorophenyl)-3-methyl-5-oxo-1,5-dihydropyrazol-4-ylidene]hydrazino}-2-hydroxy-3'-tetrazol-5-ylbiphenyl;

3-{N'-[1-(4-fluoro-3-methylphenyl)-3-methyl-5-oxo-1,5-dihydropyrazol-4-ylidene]hydrazino}-2-hydroxy-3'-tetrazol-5-ylbiphenyl;

3-{N'-[3-methyl-5-oxo-1-(4-trifluoromethylphenyl)-1,5-dihydropyrazol-4-ylidene]hydrazino}-2-hydroxy-3'-tetrazol-5-ylbiphenyl;

3'-{N'-[1-(3,4-dimethylphenyl)-3-(pyridin-4-yl-5-oxo-1,5-dihydropyrazol-4-ylidene]hydrazino}-2'-hydroxybiphenyl-3-carboxylic acid;

3-{N'-[1-(3,4-dimethylphenyl)-3-pyridin-4-yl-5-oxo-1,5-dihydropyrazol-4-ylidene]hydrazino}-2-hydroxy-3'-tetrazol-5-ylbiphenyl;

3-{N'-[1-(3,4-dimethylphenyl)-3-pyridin-2-yl-5-oxo-1,5-dihydropyrazol-4-ylidene]hydrazino}-2-hydroxy-3'-tetrazol-5-ylbiphenyl;

3'-{N'-[1-(3,4-dimethylphenyl)-3-(pyridin-2-yl-5-oxo-1,5-dihydropyrazol-4-ylidene]hydrazino}-2'-hydroxybiphenyl-3-carboxylic acid;

3-{N'-[1-(3-fluoro-4-methylphenyl)-3-methyl-5-oxo-1,5-dihydropyrazol-4-ylidene]hydrazino}-2-hydroxy-3'-tetrazol-5-ylbiphenyl;

3'-{N'-[1-(3-fluoro-4-methylphenyl)-3-methyl-5-oxo-1,5-dihydropyrazol-4-ylidene]hydrazino}-2'-hydroxybiphenyl-3-carboxylic acid;

3'-{N'-[3-methyl-5-oxo-1-(4-trifluoromethylpyrimidin-2-yl)-1,5-dihydropyrazol-4-ylidene]hydrazino}-2'-hydroxybiphenyl-3-carboxylic acid;

3'-N-tert-butoxycarbonylamino-3-{N'-[1-(3,4-Dimethylphenyl)-3-methyl-5-oxo-1,5-dihydropyrazol-4-ylidene]hydrazino}-2-hydroxybiphenyl;

3'-amino-3-{N'-[1-(3,4-dimethylphenyl)-3-methyl-5-oxo-1,5-dihydropyrazol-4-ylidene]hydrazino}-2-hydroxybiphenyl;

3-{N'-[1-(3-fluorophenyl)-3-methyl-5-oxo-1,5-dihydropyrazol-4-ylidene]hydrazino}-2-hydroxy-3'-tetrazol-5-ylbiphenyl;

3'-{N'-[1-(3-fluorophenyl)-3-methyl-5-oxo-1,5-dihydropyrazol-4-ylidene]hydrazino}-2-hydroxybiphenyl-3-carboxylic acid;

3-{N'-[3-methyl-5-oxo-1-(2,3,4,5,6-pentafluorophenyl)-1,5-dihydropyrazol-4-ylidene]hydrazino}-2-hydroxy-3'-tetrazol-5-ylbiphenyl;

3'-{N'-[3-methyl-5-oxo-1-(2,3,4,5,6-pentafluorophenyl)-1,5-dihydropyrazol-4-ylidene]hydrazino}-2'-hydroxybiphenyl-3-carboxylic acid;

3'-{N'-[1-(3,4-difluorophenyl)-3-methyl-5-oxo-1,5-dihydropyrazol-4-ylidene]hydrazino}-2'-hydroxybiphenyl-3-carboxylic acid;

3'-{N'-[1-(3,4-dimethylphenyl)-3-methoxymethyl-5-oxo-1,5-dihydropyrazol-4-ylidene]hydrazino}-2'-hydroxybiphenyl-3-carboxylic acid;

3-{N'-[1-(3,4-dimethylphenyl)-3-methoxymethyl-5-oxo-1,5-dihydropyrazol-4-ylidene]hydrazino}-2-hydroxy-3'-tetrazol-5-ylbiphenyl;

3-{N'-[1-(3,4-difluorophenyl)-3-methyl-5-oxo-1,5-dihydropyrazol-4-ylidene]hydrazino}-2-hydroxy-3'-tetrazol-5-ylbiphenyl;

3'-{N'-[1-(3,4-dimethylphenyl)-5-oxo-3-trifluoromethyl-1,5-dihydropyrazol-4-ylidene]hydrazino}-2'-hydroxybiphenyl-3-carboxylic acid;

3'-{N'-[1-(3,4-dimethylphenyl)-3-methyl-5-oxo-1,5-dihydropyrazol-4-ylidene]hydrazino}-6-fluoro-2'-hydroxybiphenyl-3-carboxylic acid;

3'-{N'-[1-(3,4-dimethylphenyl)-5-oxo-3-propyl-1,5-dihydropyrazol-4-ylidene]hydrazino}-2'-hydroxybiphenyl-3-carboxylic acid;

3-{N'-[1-(3,4-dimethylphenyl)-5-oxo-3-propyl-1,5-dihydropyrazol-4-ylidene]hydrazino}-2-hydroxy-3'-tetrazol-5-ylbiphenyl;

3'-{N'-[1-(3,4-dimethylphenyl)-3-(1-methyl-1H-pyrrol-3-yl)-5-oxo-1,5-dihydropyrazol-4-ylidene]hydrazino}-2'-hydroxybiphenyl-3-carboxylic acid;

3-{N'-[1-(3,4-dimethylphenyl)-3-(1-methyl-1H-pyrrol-3-yl)-5-oxo-1,5-dihydropyrazol-4-ylidene]hydrazino}-2-hydroxy-3'-tetrazol-5-ylbiphenyl;

3'-{N'-[1-(3,4-dimethylphenyl)-3-furan-2-yl-5-oxo-1,5-dihydropyrazol-4-ylidene]hydrazino}-2'-hydroxybiphenyl-3-carboxylic acid;

3-{N'-[1-(3,4-dimethylphenyl)-3-furan-2-yl-5-oxo-1,5-dihydropyrazol-4-ylidene]hydrazino}-2-hydroxy-3'-tetrazol-5-ylbiphenyl;

N-(2'-hydroxy-3'-{N'-[3-methyl-5-oxo-1-(4-trifluoromethyl-phenyl)-1,5-dihydro-pyrazol-4-ylidene]hydrazino}biphenyl-3-yl)-1,1,1-trifluoromethanesulfonamide;

N-(2'-hydroxy-3'-{N'-[1-(3-fluoro-4-methylphenyl)-3-methyl-5-oxo-1,5-dihydro-pyrazol-4-ylidene]hydrazino}biphenyl-3-yl)-1,1,1-trifluoromethanesulfonamide;

N-(2'-hydroxy-3'-{N'-[1-(4-fluoro-3-methylphenyl)-3-methyl-5-oxo-1,5-dihydro-pyrazol-4-ylidene]hydrazino}biphenyl-3-yl)-1,1,1-trifluoromethanesulfonamide;

N-(2'-hydroxy-3'-{N'-[1-(3,4-difluorophenyl)-3-methyl-5-oxo-1,5-dihydro-pyrazol-4-ylidene]hydrazino}biphenyl-3-yl)-1,1,1-trifluoromethanesulfonamide;

N-(3'-{N'-[1-(3,4-dimethylphenyl)-3-methyl-5-oxo-1,5-dihydropyrazol-4-ylidene]hydrazino}-2'-hydroxybiphenyl-3-yl)guanidine;

3'-{N'-[1-(3,4-dimethylphenyl)-3-ethyl-5-oxo-1,5-dihydropyrazol-4-ylidene]hydrazino}-2'-hydroxybiphenyl-3-carboxylic acid;

3-{N'-[1-(3,4-dimethylphenyl)-3-ethyl-5-oxo-1,5-dihydropyrazol-4-ylidene]hydrazino}-2-hydroxy-3'-tetrazol-5-ylbiphenyl;

3'-{N'-[1-(3,4-dimethylphenyl)-5-oxo-3-thien-2-yl-1,5-dihydropyrazol-4-ylidene]hydrazino}-2'-hydroxybiphenyl-3-carboxylic acid;

3'-{N'-[3-cyclopropyl-1-(3,4-dimethylphenyl)-5-oxo-1,5-dihydropyrazol-4-ylidene]hydrazino}-2'-hydroxybiphenyl-3-carboxylic acid;

3'-{N'-[1-(3,4-dimethylphenyl)-5-oxo-3-thiazol-2-yl-1,5-dihydropyrazol-4-ylidene]hydrazino}-2'-hydroxybiphenyl-3-carboxylic acid;

3'-{N'-[1-(3,4-dimethylphenyl)-5-oxo-1,5-dihydropyrazol-4-ylidene]hydrazino}-2'-hydroxybiphenyl-3-carboxylic acid;

3'-{N'-[1-(3,4-dimethylphenyl)-3-(1-methylethyl)-5-oxo-1,5-dihydropyrazol-4-ylidene]hydrazino}-2'-hydroxybiphenyl-3-carboxylic acid;

3'-{N'-[3-(benzyloxymethyl)-1-(3,4-dimethylphenyl)-5-oxo-1,5-dihydropyrazol-4-ylidene]hydrazino}-2'-hydroxybiphenyl-3-carboxylic acid;

3'-{N'-[3-ethyl-5-oxo-1-(4-trifluoromethylphenyl)-1,5-dihydropyrazol-4-ylidene]hydrazino}-2'-hydroxybiphenyl-3-carboxylic acid;

3'-{N'-[5-oxo-1-(4-trifluoromethylphenyl)-1,5-dihydropyrazol-4-ylidene]hydrazino}-2'-hydroxybiphenyl-3-carboxylic acid;

3'-{N'-[-1-(3,4-dimethylphenyl)-3-hydroxymethyl-5-oxo-1,5-dihydropyrazol-4-ylidene]hydrazino}-2'-hydroxybiphenyl-3-carboxylic acid;

3'-{N'-[3-benzyloxymethyl-5-oxo-1-(4-trifluoromethylphenyl)-1,5-dihydropyrazol-4-ylidene]hydrazino}-2'-hydroxybiphenyl-3-carboxylic acid;

3'-{N'-[-1-(3,4-dimethylphenyl)-3-methylsulfanylmethyl-5-oxo-1,5-dihydropyrazol-4-ylidene]hydrazino}-2'-hydroxybiphenyl-3-carboxylic acid;

3'-{N'-[-1-(3,4-dimethylphenyl)-5-oxo-3-thiophen-3-yl-1,5-dihydropyrazol-4-ylidene]hydrazino}-2'-hydroxybiphenyl-3-carboxylic acid;

3'-{N'-[5-oxo-1-(4-trifluoromethylphenyl)-3-thiophen-3-yl-1,5-dihydropyrazol-4-ylidene]hydrazino}-2'-hydroxybiphenyl-3-carboxylic acid;

3'-{N'-[5-oxo-1-(4-trifluoromethylphenyl)-3-methylsulfanylmethyl-1,5-dihydropyrazol-4-ylidene]hydrazino}-2'-hydroxybiphenyl-3-carboxylic acid;

N-(3'-{N'-[1-(3,4-dimethylphenyl)-3-methyl-5-oxo-1,5-dihydro-pyrazol-4-ylidene]hydrazino}-2'-hydroxybiphenyl-3-yl)methanesulfonamide;

3'-{N'-[1-benzo[1,3]dioxol-5-yl-3-methyl-5-oxo-1,5-dihydropyrazol-4-ylidene]hydrazino}-2'-hydroxybiphenyl-3-carboxylic acid;

3'-{N'-[1-(3,5-dimethylphenyl)-3-methyl-5-oxo-1,5-dihydropyrazol-4-ylidene]hydrazino}-2'-hydroxybiphenyl-3-carboxylic acid;

3'-{N'-[1-(3,4-dimethylphenyl)-3-methyl-5-oxo-1,5-dihydropyrazol-4-ylidene]hydrazino}-4'-hydroxybiphenyl-4-carboxylic acid;

3'-{N'-[1-(3-chloro-4-methylphenyl)-3-methyl-5-oxo-1,5-dihydropyrazol-4-ylidene]hydrazino}-2'-hydroxybiphenyl-3-carboxylic acid;

3'-{N'-[1-(3,4-dimethylphenyl)-3-methyl-5-oxo-1,5-dihydropyrazol-4-ylidene]hydrazino}-4'-hydroxybiphenyl-3-carboxylic acid;

3'-{N'-[1-(3,4-dimethylphenyl)-3-methyl-5-oxo-1,5-dihydropyrazol-4-ylidene]hydrazino}-2'-hydroxybiphenyl-3-phosphonic acid;

3'-{N'-[1-(3,4-dimethylphenyl)-3-methyl-5-oxo-1,5-dihydropyrazol-4-ylidene]hydrazino}-2'-hydroxybiphenyl-3,4-dicarboxylic acid;

2',6-dihydroxy-3'-{N'-[1-(3,4-dimethylphenyl)-3-methyl-5-oxo-1,5-dihydropyrazol-4-ylidene]hydrazino}biphenyl-3-carboxylic acid;

4-aza-3'-{N'-[1-(3,4-dimethylphenyl)-3-methyl-5-oxo-1,5-dihydropyrazol-4-ylidene]hydrazino}-2'-hydroxybiphenyl-5-carboxylic acid;

3'-{N'-[1-(3,4-dimethylphenyl)-5-oxo-1,5-dihydropyrazol-4-ylidene]hydrazino}-2'-hydroxybiphenyl-3-carboxylic acid;

3'-{N'-[1-(3,4-dimethylphenyl)-3-methyl-5-oxo-1,5-dihydropyrazol-4-ylidene]hydrazino}-2'-hydroxybiphenyl-3-sulfonic acid; and 5-(3'-{N'-[1-(3,4-Dimethylphenyl)-3-methyl-5-oxo-1,5-dihydropyrazol-4-ylidene]hydrazino}-2'-hydroxybiphenyl-3-ylmethylene)thiazolidine-2,4-dione;

and pharmaceutically acceptable salts, hydrates, solvates and esters thereof.

Compounds of Formula (I) are included in the pharmaceutical compositions of the invention and used in the methods of the invention.

By the term "protected hydroxy" or "protected —OH" as used herein, is meant the alcoholic or carboxylic-OH groups which can be protected by conventional blocking groups in the art such as described in "Protective Groups In Organic Synthesis" by Theodora W. Greene, Wiley-Interscience, 1981, New York. Compounds containing protected hydroxy groups may also be useful as intermediates in the preparation of the pharmaceutically active compounds of the invention.

By the term "aryl" as used herein, unless otherwise defined, is meant a cyclic or polycyclic aromatic ring containing from 1 to 14 carbon atoms and optionally containing from one to five heteroatoms, provided that when the number of carbon atoms is 1 the aromatic ring contains at least four heteroatoms, when the number of carbon atoms is 2 the aromatic ring contains at least three heteroatoms, when the number of carbons is 3 the aromatic ring contains at least two heteroatoms and when the number of carbon atoms is 4 the aromatic ring contains at least one heteroatom.

By the term "$C_1$–$C_{12}$aryl" as used herein, unless otherwise defined, is meant phenyl, naphthalene, 3,4-methylenedioxyphenyl, pyridine, biphenyl, quinoline, pyrimidine, quinazoline, thiophene, furan, pyrrole, pyrazole, imidazole and tetrazole.

When referring to compounds of Formula (I) and (II), the term "substituted" as used herein, unless otherwise defined, is meant that the subject chemical moiety has one or more substituents selected from the group consisting of: —$CO_2R^{20}$, aryl, —$C(O)NHS(O)_2R^{20}$, —$NHS(O)_2R^{20}$, hydroxyalkyl, alkoxy, —$C(O)NR^{21}R^{22}$, acyloxy, alkyl, amino, N-acylamino, hydroxy, —$(CH2)_gC(O)OR^8$, —$S(O)_nR^8$, nitro, tetrazole, cyano, oxo, halogen, trifluoromethyl, protected —OH and a heterocyclic methylene substituent as represented by Formula (III),

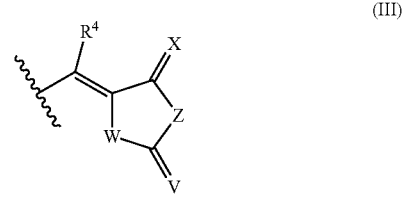

(III)

where g is 0–6; $R^8$ is hydrogen or alkyl; $R^{20}$ is selected form hydrogen, $C_1$–$C_4$alkyl, aryl and trifluoromethyl; $R^{21}$ and $R^{22}$ are independently selected form hydrogen, $C_1$–$C_4$alkyl, aryl and trifluoromethyl; V, W, X and Z are each independently selected from O, S, and $NR^{16}$, where $R^{16}$ is selected from: hydrogen, alkyl, cycloalkyl, $C_1$–$C_{12}$aryl, substituted alkyl, substituted cycloalkyl and substituted $C_1$–$C_{12}$aryl; and n is 0–2.

When referring to compounds of Formula (V) and (VI), the term "substituted" as used herein, unless otherwise defined, is meant that the subject chemical moiety has one or more substituents selected from the group consisting of: —$CO_2R^{20}$, aryl, —$C(O)NHS(O)_2R^{20}$, —$NHS(O)_2R^{20}$, hydroxyalkyl, alkoxy, —$C(O)NR^{21}R^{22}$, acyloxy, alkyl, amino, N-acylamino, hydroxy, —$(CH2)_gC(O)OR^8$, —$S(O)_nR^8$, nitro, tetrazole, cyano, oxo, halogen, trifluoromethyl and protected —OH, where g is 0–6, $R^8$ is hydrogen or alkyl, $R^{20}$ is selected form hydrogen, $C_1$–$C_4$alkyl, aryl and trifluoromethyl, and $R^{21}$ and $R^{22}$ are independently selected form hydrogen, $C_1$–$C_4$alkyl, aryl and trifluoromethyl, and n is 0–2.

By the term "alkoxy" as used herein is meant —Oalkyl where alkyl is as described herein including —$OCH_3$ and —$OC(CH_3)_2CH_3$.

The term "cycloalkyl" as used herein unless otherwise defined, is meant a nonaromatic, unsaturated or saturated, cyclic or polycyclic $C_3$–$C_{12}$.

Examples of cycloalkyl and substituted cycloalkyl substituents as used herein include: cyclohexyl, 4-hydroxycyclohexyl, 2-ethylcyclohexyl, propyl 4-methoxycyclohexyl, 4-methoxycyclohexyl, 4-carboxycyclohexyl, cyclopropyl and cyclopentyl.

By the term "acyloxy" as used herein is meant —OC(O)alkyl where alkyl is as described herein. Examples of acyloxy substituents as used herein include: —$OC(O)CH_3$, —$OC(O)CH(CH_3)_2$ and —$OC(O)(CH_2)_3CH_3$.

By the term "N-acylamino" as used herein is meant —N(H)C(O)alkyl, where alkyl is as described herein. Examples of N-acylamino substituents as used herein include: —N(H)C(O)CH$_3$, —N(H)C(O)CH(CH$_3$)$_2$ and —N(H)C(O)(CH$_2$)$_3$CH$_3$.

By the term "aryloxy" as used herein is meant -Oaryl where aryl is phenyl, naphthyl, 3,4-methylenedioxyphenyl, pyridyl or biphenyl optionally substituted with one or more substituents selected from the group consisting of: alkyl, hydroxyalkyl, alkoxy, trifuloromethyl, acyloxy, amino, N-acylamino, hydroxy, —(CH2)$_g$C(O)OR$^8$, —S(O)$_n$R$^8$, nitro, cyano, halogen and protected —OH, where g is 0–6, R$^8$ is hydrogen or alkyl, and n is 0–2. Examples of aryloxy substituents as used herein include: phenoxy, 4-fluorophenyloxy and biphenyloxy.

By the term "heteroatom" as used herein is meant oxygen, nitrogen or sulfur.

By the term "halogen" as used herein is meant a substituent selected from bromide, iodide, chloride and fluoride.

By the term "alkyl" and derivatives thereof and in all carbon chains as used herein is meant a linear or branched, saturated or unsaturated hydrocarbon chain, and unless otherwise defined, the carbon chain will contain from 1 to 12 carbon atoms. Examples of alkyl substituents as used herein include: —CH$_3$, —CH$_2$—CH$_3$, —CH$_2$—CH$_2$—CH$_3$, —CH(CH$_3$)$_2$, —C(CH$_3$)$_3$, —(CH$_2$)$_3$—CH$_3$, —CH$_2$—CH(CH$_3$)$_2$, —CH(CH$_3$)—CH$_2$—CH$_3$, —CH=CH$_2$, and —C.C—CH$_3$.

By the term "treating" and derivatives thereof as used herein, is meant prophylatic and therapeutic therapy.

All publications, including but not limited to patents and patent applications, cited in this specification are herein incorporated by reference as though fully set forth.

Compounds of Formula (I) are included in the pharmaceutical compositions of the invention and used in the methods of the invention. Where a —COOH or —OH group is present, pharmaceutically acceptable esters can be employed, for example methyl, ethyl, pivaloyloxymethyl, and the like for —COOH, and acetate maleate and the like for —OH, and those esters known in the art for modifying solubility or hydrolysis characteristics, for use as sustained release or prodrug formulations.

The novel compounds of Formulas I and II are prepared as shown in Schemes I to IV below, or by analogous methods, wherein the 'R' substituents, AR, Y and m are as defined in Formulas I and II respectively and provided that the 'R' and m substituents, AR and Y do not include any such substituents that render inoperative the processes of Schemes I to IV. All of the starting materials are commercially available or are readily made from commercially available starting materials by those of skill in the art.

Scheme I

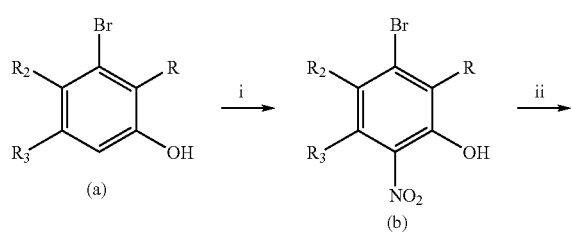

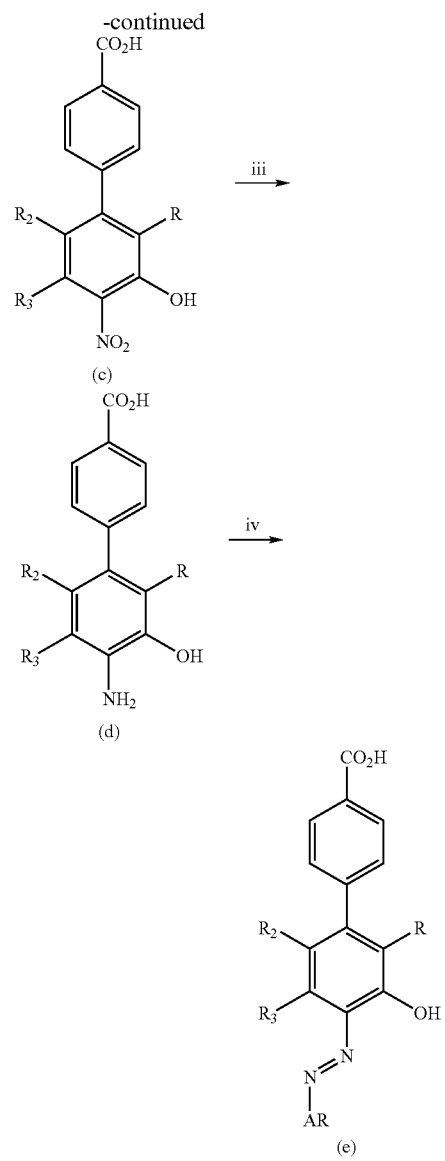

i), nitric acid; sulfuric acid; ii) 4-carboxyphenylboronic acid; Pd(PPh$_3$)$_4$, Na2CO3, dioxane, water; iii) H$_2$, Pd—C; iv) NaNO$_2$, AR, NaHCO$_3$, water, EtOH Scheme I outlines the formation of Formula I compounds. As used in scheme I, a 3-bromophenol (a) is nitrated with nitric acid or sodium nitrate and sulfuric acid to give nitro phenol (b). Coupling of (b) with a substituted arylboronic acid, such as 3-carboxyphenylboronic acid or 4-carboxyphenylboronic acid in the presence of a catalyst, preferably tetrakistriphenylphosphino palladium and a base such as sodium carbonate ot triethylamine in a suitable solvent such as aqueous 1,4-dioxane or dimethylformnamide afforded substituted aryl compound (c). Reduction of the nitro group by catalytic hydrogenation or mediated by a reducing metal such as iron of tin dichloride in a suitable solvent such as ethanol, acetic acid or water gives the aniline (d). Compound (d) is diazotized by reaction with sodium nitrite and an appropriate acid, such as nitric acid, sulfuric acid or, preferably, hydrochloric acid, in an appropriate aqueous solvent, such as water or, preferably an ethanol-water mixture to produce a diazonium species which is directly converted to compoud (e) in a coupling reaction with an appropriate aryl species in the presence of a base, preferably sodium hydrogen carbonate, or an acid, preferably hydrochloric acid.

Scheme II

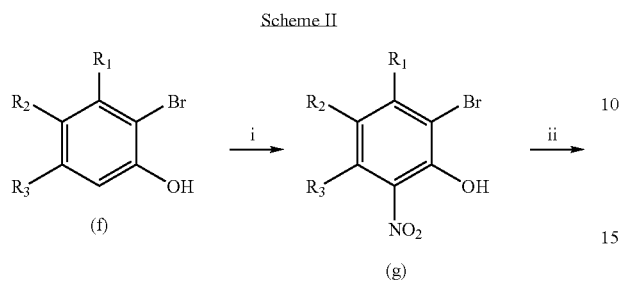

(f)   (g)

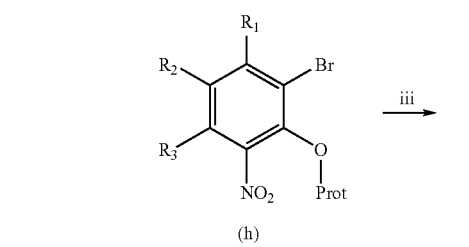

(h)

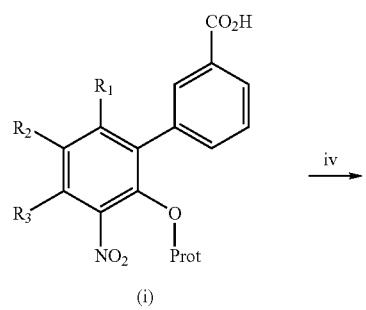

(i)

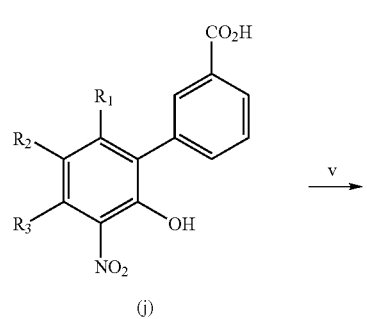

(j)

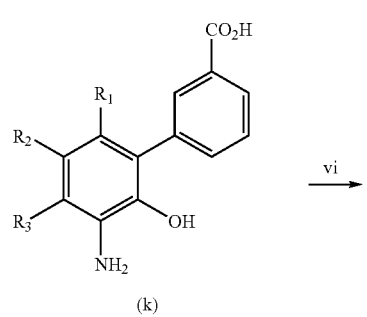

(k)

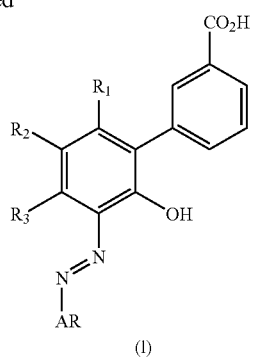

(l)

i), $NaNO_2$, sulfuric acid; ii), MeI, $K_2CO_3$, acetone; iii) 3-carboxyphenylboronic acid; $Pd(PPh_3)_4$, Na2CO3, dioxane, water; iv) 48% aqu. HBr, AcOH; v) $H_2$, Pd—C; vi) $NaNO_2$, AR, $NaHCO_3$, water, EtOH Scheme II outlines an alternative synthesis of Formula I compounds. A 2-bromophenol (f) (such as 2-bromophenol or 2-bromo-5-methylphenol is nitrated with nitric acid or sodium nitrate and sulfuric acid, to give nitro compound (g). The phenol (g) is then protected by reaction with an alkylating agent such as benzyl bromide or preferably methyl iodide in the presence of a base such as sodium hydride or potassium carbonate in a suitable solvent such as dimethylformamide, tetrahydrofuran or acetone to give protected nitrophenol (h) (Prot=alkyl or substituted alkyl, e.g. methyl, benzyl). Coupling of (h) with a substituted arylboronic acid, such as 3-carboxyphenylboronic acid or 4-carboxyphenylboronic acid, in the presence of a catalyst, preferably tetrakistriphenylphosphino palladium and a base such as sodium carbonate ot triethylamine in a suitable solvent such as aqueous 1,4-dioxane or dimethylformamide afforded substituted aryl compound (i). Removal of the protecting group (Prot) is accomplished using an protic or Lewis acid; such as concentrated hydrobromic acid, boron tribromide or trimethylsilyl iodide to affored the phenol (j). Reduction of the nitro group by catalytic hydrogenation or mediated by a reducing metal such as iron of tin dichloride in a suitable solvent such as ethanol, acetic acid; or water gives the aniline (k). Compound (k) is diazotized by reaction with sodium nitrite and an appropriate acid, such as nitric acid, sulfuric acid or, preferably, hydrochloric acid, in an appropriate aqueous solvent, such as water or, preferably, an ethanol-water mixture to produce a diazonium species which is directly converted to compoud (i) in a coupling reaction with an appropriate aryl species in the presence of a base, preferably sodium hydrogen carbonate, or an acid, preferably hydrochloric acid.

Scheme III

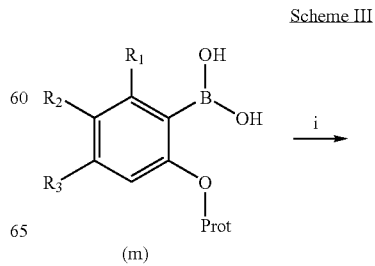

(m)

-continued

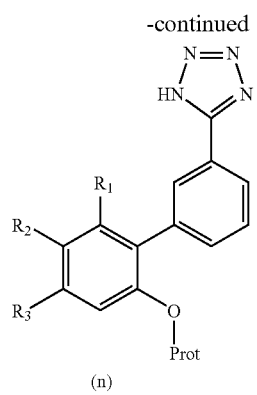

(n)

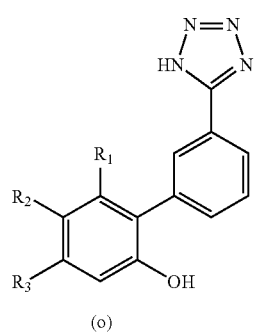

(o)

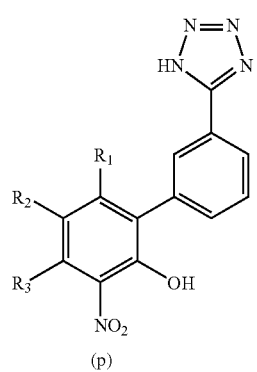

(p)

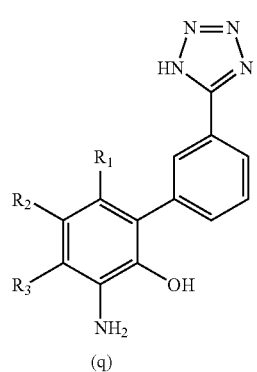

(q)

-continued

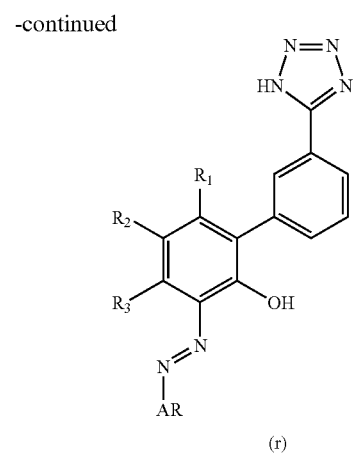

(r)

i) 5-(3-bromophenyl)tetrazole, Pd(PPh$_3$)$_4$, Na2CO3, dioxane, water; ii) 48% aqu. HBr, AcOH; iii) HNO$_2$, AcOH; iv) H$_2$, Pd—C; v) NaNO$_2$, AR, NaHCO$_3$, water, EtOH Scheme II outline a further procedure for the synthesis of Formula I compounds. A protected hydroxyphenylboronic acid; (m) (Prot=alkyl or substituted alkyl, e.g. methyl, benzyl) such as 5-chloro-2-methoxyphenylboronic acid, 5-fluoro-2-methoxyphenyl, boronic acid or 2-methoxy-5-formylphenylboronic acid, is coupled with a substituted halogenoaryl species, such as 5-(3-bromophenyl)tetrazole or 5-bromonicotinic acid, in the presence of a catalyst, preferably tetrakistriphenylphosphino palladium, and a base, such as sodium carbonate or triethylamine in a suitable solvent such as aqueous 1,4-dioxane or dimethylformamide afforded substituted aryl compound (n). Removal of the protecting group Prot is accomplished using an protic or Lewis acid, such as concentrated hydrobromic acid, boron tribromide or trimethylsilyl iodide to afford the phenol (o). Nitration of (o) with nitric acid, or sodium nitrate in the presence of an acid, such as acetic or hydrochloric acid, affords the nitro compound (p). Reduction of the nitro group by catalytic hydrogenation or mediated by a reducing metal such as iron of tin dichloride in a suitable solvent such as ethanol, acetic acid or water gives the aniline (q). Compound (q) is diazotized by reaction with sodium nitrite and an appropriate acid, such as nitric acid, sulfuric acid or, preferably, hydrochloric acid, in an appropriate aqueous solvent, such as water or, preferably, an ethanol-water mixture to produce a diazonium species which is directly converted to compoud (r) in a coupling reaction with an appropriate aryl species in the presence of a base, preferably sodium hydrogen carbonate, or an acid, preferably hydrochloric acid.

Scheme IV

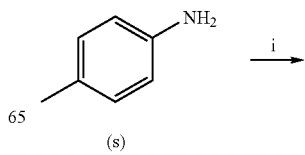

(s)

-continued

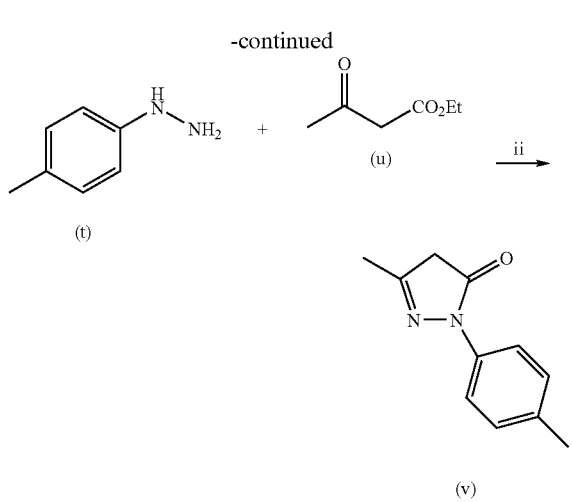

i) NaNO₂, HCl, water then SnCl₂, water;
ii) AcOH, heat

Scheme IV outlines the formation of pyrazoles for use in scheme I-III. An amine such as 4-methylaniline, compound (s), is diazotized by the action of sodium nitrite and an appropriate acid, such as hydrochloric acid, nitric acid or sulfuric acid, in an appropriate aqueous solvent system, such as water or ethanol-water mixtures, then reduced in situ by tin chloride to afford hydrazine, compound (t). The hydrazine is then condensed with a electrophilic carbonyl species such as ethyl acetoacetate (u), ethyl cyanoacetate or diethyl malonate, in an appropriate solvent such as acetic acid or ethanol at an appropriate temperature typically 0–100° to give the corresponding pyrazole, compound (v) as described herein.

In preparing the presently invented compounds of Formula (I), the following novel intermediates are prepared:
4'-Amino-3'-hydroxybiphenyl-4-carboxylic acid;
4'-Amino-3'-hydroxybiphenyl-3-carboxylic acid;
3'-Amino-2'-hydroxybiphenyl-3-carboxylic acid;
3'-Amino-2'-hydroxybiphenyl-4-carboxylic acid;
3-Amino-2-hydroxy-3'-(1H-tetrazol-5-yl)biphenyl;
3-Amino-2-hydroxy-4'-(1H-tetrazol-5-yl)biphenyl;
3-Amino-5-chloro-2-hydroxy-4'-(1H-tetrazol-5-yl)-biphenyl;
6-(3-Amino-2-hydroxyphenyl)pyridine-2-carboxylic acid;
6-(3-Amino-5-chloro-2-hydroxyphenyl)pyridine-2-carboxylic acid;
6-(3-Amino-2-hydroxy-5-methylphenyl)pyridine-2-carboxylic acid;
5-(3-Amino-2-hydroxyphenyl)nicotinic acid;
5-(3-Amino-2-hydroxy-5-methylphenyl)nicotinic acid;
2-(3-Amino-2-hydroxyphenyl)isonicotinic acid;
3'-Amino-2'-hydroxy-5'-methylbiphenyl-3-carboxylic acid;
3'-Amino-5'-fluoro-2'-hydroxybiphenyl-3-carboxylic acid;
3'-Amino-5'-chloro-2'-hydroxybiphenyl-3-carboxylic acid;
3'-Amino-2'-hydroxybiphenyl-3,5-dicarboxylic acid;
N-[1-(3'-Amino-2'-hydroxybiphenyl-3-yl)methanoyl]methanesulfonamide;
N-(3'-Amino-2'-hydroxybiphenyl-3-yl)-1,1,1-trifluoromethanesulfonamide;
(3'-Amino-2'-hydroxybiphenyl-3-yl)phosphonic acid;
3'-Amino-2'-hydroxybiphenyl-3,4-dicarboxylic acid;
3'-Amino-4,2'-dihydroxybiphenyl-3-carboxylic acid;
3'-Amino-2'-hydroxybiphenyl-3-sulfonic acid;
3'-Hydroxy-4'-nitrobiphenyl-4-carboxylic acid;
3'-Hydroxy-4'-nitrobiphenyl-3-carboxylic acid;
2'-Hydroxy-3'-nitrobiphenyl-3-carboxylic acid;
2'-Hydroxy-3'-nitrobiphenyl-4-carboxylic acid;
5-Chloro-2-hydroxy-3-nitro-3'-(1H-tetrazol-5-yl)biphenyl;
5-Chloro-2-hydroxy-3-nitro-4'-(1H-tetrazol-5-yl)biphenyl;
6-(5-Chloro-2-hydroxy-3-nitrophenyl)pyridine-2-carboxylic acid;
6-(2-Hydroxy-5-methyl-3-nitrophenyl)pyridine-2-carboxylic acid;
5-(5-Chloro-2-hydroxy-3-nitrophenyl)nicotinic acid;
5-(5-Chloro-2-hydroxy-5-methyl-3-nitrophenyl)nicotinic acid;
2-(5-Chloro-2-hydroxy-3-nitrophenyl)isonicotinic acid;
5'-Chloro-2'-hydroxy-3'-nitrobiphenyl-3-carboxylic acid;
5'-Chloro-2'-hydroxy-3'-nitrobiphenyl-3,5-dicarboxylic acid;
N-[1-(5'-Chloro-2'-hydroxy-3'-nitrobiphenyl-3-yl)methanoyl]methanesulfonamide;
1,1,1-Trifluoro-N-(2'-hydroxy-3'-nitrobiphenyl-3-yl)methanesulfonamide;
(5'-Chloro-2'-hydroxy-3'-nitrobiphenyl-3-yl)phosphonic acid;
5'-Chloro-2'-hydroxy-3'-nitrobiphenyl-3,4-dicarboxylic acid;
5'-Chloro-4,2'-dihydroxy-3'-nitrobiphenyl-3-carboxylic acid;
5'-Chloro-2'-hydroxy-3'-nitrobiphenyl-3-sulfonic acid;
2'-Methoxy-3'-nitrobiphenyl-3-carboxylic acid;
2'-Methoxy-3'-nitrobiphenyl-4-carboxylic acid;
5-Chloro-2-hydroxy-3'-(1H-tetrazol-5-yl)biphenyl;
5-Chloro-2-hydroxy-4'-(1H-tetrazol-5-yl)biphenyl;
6-(5-Chloro-2-hydroxyphenyl)pyridine-2-carboxylic acid;
6-(2-Hydroxy-5-methylphenyl)pyridine-2-carboxylic acid;
6-(2-Hydroxy-5-methylphenyl)pyridine-2-carboxylic acid;
5-(5-Chloro-2-hydroxy-5-methylphenyl)nicotinic acid;
2-(5-Chloro-2-hydroxyphenyl)isonicotinic acid;
5'-Chloro-2'-hydroxybiphenyl-3-carboxylic acid;
5'-Chloro-2'-hydroxybiphenyl-3,5-dicarboxylic acid;
N-[1-(5'-Chloro-2'-hydroxybiphenyl-3-yl)methanoyl]methanesulfonamide;
3'-Amino-3-nitrobiphenyl-2-ol;
(5'-Chloro-2'-hydroxybiphenyl-3-yl)phosphonic acid;
5'-Chloro-2'-hydroxybiphenyl-3,4-dicarboxylic acid;
5'-Chloro-4,2'-dihydroxybiphenyl-3-carboxylic acid;
5'-Chloro-2'-hydroxybiphenyl-3-sulfonic acid;
5-Chloro-2-methoxy-3'-(1H-tetrazol-5-yl)biphenyl;
5-Chloro-2-methoxy-4'-(1H-tetrazol-5-yl)biphenyl;
6-(5-Chloro-2-methoxyphenyl)pyridine-2-carboxylic acid;
6-(2-Methoxy-5-methylphenyl)pyridine-2-carboxylic acid;
6-(2-Methoxy-5-methylphenyl)pyridine-2-carboxylic acid;
5-(5-Chloro-2-methoxy-5-methylphenyl)nicotinic acid;
2-(5-Chloro-2-methoxyphenyl)isonicotinic acid;
5'-Chloro-2'-methoxybiphenyl-3-carboxylic acid;
5'-Chloro-2'-methoxybiphenyl-3,5-dicarboxylic acid;
N-[1-(5'-Chloro-2'-[methoxybiphenyl-3-yl)methanoyl]methanesulfonamide;
N-(2'-Methoxy-3'-nitrobiphenyl-3-yl)-acetamide;
(5'-Chloro-2'-methoxybiphenyl-3-yl)phosphonic acid;
5'-Chloro-2'-methoxybiphenyl-3,4-dicarboxylic acid;
5'-Chloro-4-hydroxy-2'-methoxybiphenyl-3-carboxylic acid; and
5'-Chloro-2'-methoxybiphenyl-3-sulfonic acid.

The treatment of thrombocytopenia, as described herein, is accomplished by increasing the production of platelets.

By the term "co-administering" and derivatives thereof as used herein is meant either simultaneous administration or any manner of separate sequential administration of a TPO mimetic compound, as described herein, and a further active ingredient or ingredients, known to treat thrombocytopenia, including chemotherapy-induced thrombocytopenia and bone marrow transplantation and other conditions with depressed platelet production. The term further active ingredient or ingredients, as used herein, includes any compound or therapeutic agent known to or that demonstrates advantageous properties when administered with TPO or a TPO mimetic. Preferably, if the administration is not simultaneous, the compounds are administered in a close time proximity to each other. Furthermore, it does not matter if the compounds are administered in the same dosage form, e.g. one compound may be administered topically and another compound may be administered orally.

Examples of a further active ingredient or ingredients for use in combination with the presently invented TPO mimetic compounds include but are not limited to: chemoprotective or myeloprotective agents such as G-CSF, BB10010 (Clemons et al., *Breast Cancer Res. Treatment*, 1999, 57, 127), amifostine (Ethyol) (Fetscher et al., *Current Opinion in Hemat.*, 2000, 7, 255–60), SCF, IL-11, MCP-4, IL-1-beta, AcSDKP (Gaudron et al., *Stem Cells*, 1999, 17, 100–6), TNF-a, TGF-b, MIP-1a (Egger et al., *Bone Marrow Transpl.*, 1998, 22 (Suppl. 2), 34–35), and other molecules identified as having anti-apoptotic, survival or proliferative properties.

Tpo has been demonstrated to act as a mobilizer of stem cells into the peripheral blood (Neumann T. A. et al., *Cytokines, Cell. & Mol. Ther.*, 2000, 6, 47–56). This activity can synergize with stem cell mobilizers such as G-CSF (Somolo et al., *Blood*, 1999, 93, 2798–2806). The TPO mimetic compounds of the present invention are thus useful in increasing the numbers of stem cells in circulation in donors prior to leukapheresis for hematopoietic stem-cell transplantation in patients receiving myelo-ablative chemotherapy.

Likewise, TPO stimulates growth of myeloid cells, particularly those of granulocyte/macrophage lineage (Holly et al., U.S. Pat. No. 5,989,537). Granulocyte/macrophage progenitors are cells of the myeloid lineage that mature as neutrophils, monocytes, basophils and eosinophils. The compounds described in the present invention have thus therapeutic utility in stimulating the poliferation of neutrophils in patients with neutropenic conditions.

Additional examples of a further active ingredient or ingredients for use in combination with the presently invented TPO mimetic compounds include but are not limited to: stem cell, megakaryocyte, neutrophil mobilizers such as chemotherapeutic agents (i.e., cytoxan, etoposide, cisplatin, Ballestrero A. et al., *Oncology*, 2000, 59, 7–13), chemokines, IL-8, Gro-beta (King, A. G. et al. *J. Immun.*, 2000, 164, 3774–82), receptor agonist or antagonist antibodies, small molecule cytokine or receptor agonists or antagonists, SCF, Flt3 ligand, adhesion molecule inhibitors or antibodies such as: anti-VLA-4 (Kikuta T. et al., *Exp. Hemat.*, 2000, 28, 311–7) or anti-CD44 (Vermeulen M. et al., *Blood*, 1998, 92, 894–900), cytokine/chemokine/interleukin or receptor agonist or antagonist antibodies, MCP-4 (Berkhout T A., et al., *J. Biol. Chem.*, 1997, 272, 16404–16413; Uguccioni M. et al., *J. Exp. Med.*, 1996, 183, 2379–2384).

Because the pharmaceutically active compounds of the present invention are active as TPO mimetics they exhibit therapeutic utility in treating thrombocytopenia and other conditions with depressed platelet production.

By the term "thrombocytopenia" and derivatives thereof as used herein is to be broadly interpreted as any decrease in the number of blood platelets below what is considered normal or desired for a healthy individual. Thrombocytopenia is known to have many causative factors, including but not limited to, radiation therapy, chemotherapy, immune therapy, immune thrombocytopenic purpura (ITP, Bussel J. B., *Seminars in Hematology*, 2000, 37, Suppl 1, 1–49), myelodysplastic syndrom (MDS), aplastic anemia, AML, CML, viral infections (including, but not limited to; HIV, hepatitis C, parvovirus) liver disease, myeloablation, bone marrow transplant, stem cell transplant, peripheral blood stem cell transplant, progenitor cell defect, polymorphisms in stem cells and progenitor cells, defects in Tpo, neutropenia (Sawai, N. J. *Leukocyte Biol.*, 2000, 68, 137–43), dendritic cell mobilization (Kuter D. J. *Seminars in Hematology*, 2000, 37, Suppl 4, 41–49), proliferation, activation or differentiation. The pharmaceutically active compounds of this invention are useful in treating thrombocytopenia regardless of the factor or factors causing the condition. The pharmaceutically active compounds of this invention are also useful in treating thrombocytopenia when the causative factor or factors of the condition are unknown or have yet to be identified.

Prophylactic use of the compounds of this invention is contemplated whenever a decrease in blood or blood platelets is anticipated. Prophylactic use of the compounds of this invention results in a build up of platelets or a commencement of platelet production prior to an anticipated loss of blood or blood platelets. Prophylactic uses of the compounds of this invention includes but is not limited to transplant surgery, surgery, anesthesia prior to child birth and gut protection.

Human dendritic cells have been shown to express the TPO receptor (Kumamoto et al., *Br. J. Haem*, 1999, 105, 1025–1033) and TPO is a potent mobilizer of dendritic cells. The TPO mimetic compounds of the current invention are also useful as a vaccine adjuvant in that they increase the activity and mobility of dendritic cells. The pharmaceutically active compounds of this invention are useful as an immunological adjuvant, given in combination with an orally, transdermally or subcutaneously delivered vaccine and/or immunomodulator, by increasing the activity and mobility of dendritic cells.

Tpo is known to have various effects including anti-apototic/survival effects on megakaryocytes, platelets and stem cells, and proliferative effects on stem cells and megakaryocytic cells (Kuter D. J. Seminars in Hematology, 2000, 37, 41–9). These Tpo activities effectively increase the number of stem and progenitor cells so that there is synergistic effects when Tpo is used in conjunction with other cytokines that induce differentiation.

The TPO mimetic compounds of the current invention are also useful in acting on cells for survival or proliferation in conjunction with other agents known to act on cells for survival or proliferation. Such other agents include but are not limited to: G-CSF, GM-CSF, TPO, M-CSF, EPO, Gro-beta, IL-11, SCF, FLT3 ligand, LIF, IL-3, IL-6, IL-1, Progenipoietin, NESP, SD-01, or IL-5 or a biologically active derivative of any of the aforementioned agents, KT6352 (Shiotsu Y. et al., *Exp. Hemat.* 1998, 26, 1195–1201), uteroferrin (Laurenz J C., et al. *Comp. Biochem. & Phys., Part A. Physiology.*, 1997, 116, 369–77), FK23 (Hasegawa T., et al. *Int. J. Immunopharm.*, 1996, 18 103–112) and other molecules identified as having anti-apoptotic, survival or proliferative properties for stem cells, progenitor cells, or other cells expressing Tpo Receptors.

In determining potency as TPO mimetics, the following assays were employed:

Luciferase Assay

Compounds of the present invention were tested for potency as mimetics of the TPO receptor in a Luciferase assay such as described in Lamb, et al., *Nucleic Acids Research* 23: 3283–3289 (1995) and Seidel, et al., *Proc. Natl. Acad. Sci., USA* 92: 3041–3045 (1995) by substituting a TPO-responsive BaF3 cell line (Vigon et al. *Proc. Natl. Acad. Sci. USA* 1992, 89, 5640–5644) for the HepG2 cells utilized therein. The murine BaF3 cells express TPO receptors and closely match the pattern of STAT (signal transducers and activators of transcription) activation observed in primary murine and human bone marrow cells.

Proliferation Assay

Some of the more preferred compounds of this invention were active in an in vitro proliferation assay using the human UT7TPO cell line. UT7TPO cells are a human megakaryoblastic cell line that express Tpo-R, whose survival and growth is dependent on the presence of TPO (Komatsu et al. *Blood* 1996, 87,4552).

Differentiation Assay

Likewise, some of the most preferred compounds of this invention were also positive in stimulating the maturation of megakaryocytes from human bone marrow cells. In this assay, purified human CD34+ progenitor cells were incubated in liquid culture with test compounds for 10 days and the number of cells expressing the transmembrane glycoprotein CD41 (gpIIb), a megakaryocytic marker, was then measured by flow cytometry (see Cwirla, S. E. et al *Science*, 1997, 276, 1696).

The pharmaceutically active compounds within the scope of this invention are useful as TPO mimetics in mammals, particularly humans, in need thereof.

Some of the preferred compounds within the scope of the invention showed activation from about 4% to 100% control at a concentration of 0.001–10 uM in the luciferase assay. The preferred compounds of the invention also promoted the proliferation of MT7TPO and 32D-mpl cells at a concentration of 0.003 to 30 uM. The preferred compounds of the invention also showed activity in the CD41 megakaryocytic assay at a concentration of 0.003 to 30 uM.

The present invention therefore provides a method of treating thrombocytopenia and other conditions with depressed platelet production, which comprises administering a compound of Formula (I) or a pharmaceutically acceptable salt, hydrate, solvate or ester thereof in a quantity effective to enhance platelet production. The compounds of Formula (I) also provide for a method of treating the above indicated disease states because of their demonstrated ability to act as TPO mimetics. The drug may be administered to a patient in need thereof by any conventional route of administration, including, but not limited to, intravenous, intramuscular, oral, subcutaneous, intradermal, and parenteral.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid;. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparation are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001–100 mg/kg of active compound, preferably 0.001–50 mg/kg. When treating a human patient in need of a TPO mimetic, the selected dose is administered preferably from 1–6 times daily, orally or parenterally. Preferred forms of parenteral administration include topically, rectally, transdermally, by injection and continuously by infusion. Oral dosage units for human administration preferably contain from 0.05 to 3500 mg of active compound. Oral administration, which uses lower dosages is preferred. Parenteral administration, at high dosages, however, also can be used when safe and convenient for the patient.

Optimal dosages to be administered may be readily determined by those skilled in the art, and will vary with the particular TPO mimetic in use, the strength of the preparation, the mode of administration, and the advancement of the disease condition. Additional factors depending on the particular patient being treated will result in a need to adjust dosages, including patient age, weight, diet, and time of administration.

The method of this invention of inducing TPO mimetic activity in mammals, including humans, comprises administering to a subject in need of such activity an effective TPO mimetic amount of a pharmaceutically active compound of the present invention.

The invention also provides for the use of a compound of Formula (I) in the manufacture of a medicament for use as a TPO mimetic.

The invention also provides for the use of a compound of Formula (I) in the manufacture of a medicament for use in therapy.

The invention also provides for the use of a compound of Formula (I) in the manufacture of a medicament for use in enhancing platelet production.

The invention also provides for the use of a compound of Formula (I) in the manufacture of a medicament for use in treating thrombocytopenia.

The invention also provides for a pharmaceutical composition for use as a TPO mimetic which comprises a compound of Formula (I) and a pharmaceutically acceptable carrier.

The invention also provides for a pharmaceutical composition for use in the treatment of thrombocytopenia which comprises a compound of Formula (I) and a pharmaceutically acceptable carrier.

The invention also provides for a pharmaceutical composition for use in enhancing platelet production which comprises a compound of Formula (I) and a pharmaceutically acceptable carrier.

No unacceptable toxicological effects are expected when compounds of the invention are administered in accordance with the present invention.

In addition, the pharmaceutically active compounds of the present invention can be co-administered with further active ingredients, such as other compounds known to treat thrombocytopenia, including chemotherapy-induced thrombocytopenia and bone marrow transplantation and other conditions with depressed platelet production, or compounds known to have utility when used in combination with a TPO mimetic.

Contemplated Equivalents—It will be appreciated by the person of ordinary skill in the art that the compounds of Formulas I and II may also exist in tautomeric forms. For example, in Formula I, the double bond that is drawn between the two nitrogen atoms exists between the lower nitrogen atom and the AR substituent. Tautomeric forms of the compounds of Formulas I and II are exemplified by the following Formula (IV):

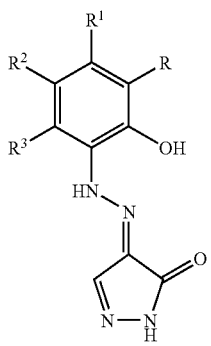

where the 'R' groups are as defined above. All such compounds are included in the scope of the invention and inherently included in the definition of the compounds of Formulas I and II.

Without further elaboration, it is believed that one skilled in the art can, using the preceding description, utilize the present invention to its fullest extent. The following Examples are, therefore, to be construed as merely illustrative and not a limitation of the scope of the present invention in any way.

Experimental Details

EXAMPLE 1

Preparation of 4'-{N'-[1-(3,4-dimethylphenyl)-3-methyl-5-oxo-1,5-dihydropyrazol-4-ylidene]hydrazino}-3'-hydroxybiphenyl-4-carboxylic acid a) 5-bromo-2-nitrophenol 3-Bromophenol (32.9 g, 0.19 mol) was added slowly to a cold (10° C.) solution of sodium nitrate (29.0 g, 0.34 mol) in conc. sulfuric acid; (40.0 g) and water (70.0 mL) and the resulting mixture was allowed to stir at room temperature for 2 h. Water (200 mL) was added and the resulting mixture was extracted with diethyl ether and the extract was dried ($MgSO_4$), filtered and concentrated. The residue was purified by flash chromatography (silica gel, 10% ethyl acetate/hexanes) to afford first the title compound (8.1 g, 20%), mp 40–42° C., then the undesired isomer, 3-bromo-4-nitrophenol, as a yellow solid (12.7 g, 31%). mp 125–127° C.

b) 3'-hydroxy-4'-nitrobiphenyl-4-carboxylic acid;

A solution of the compound from Example 1a) (2.18 g, 0.01 mol.), 4-carboxyphenylboronic acid; (1.74 g, 0.0105 mol.), 2M aqu. sodium carbonate (10.0 mL; 0.02 mol.) and tetrallistriphenylphosphino palladium(0) (0.5 g) in 1,4-dioxane (60.0 mL) was stirred and heated under reflux under a nitrogen atmosphere for 24 h.

The reaction mixture was cooled and evaporated and the residue treated with 6M aqu. hydrochloric acid; (100 mL). The grey precipitate was filtered and washed well with water then diethyl ether to afford the title compound (2.3 g; 88%) as a colorless solid. $^1$H NMR (300 MHz, $d_6$-DMSO) δ 13.5–10.5 (br s, 2H), 8.06 (d, J=8.4 Hz, 2H), 8.03 (d, J=8.6 Hz, 1H), 7.83 (d, J=8.4 Hz, 1H), 7.45 (d, J=1.8 Hz, 1H), 7.35 (dd, J=8.6, 1.8 Hz, 1H).

c) 4'-amino-3'-hydroxybiphenyl-4-carboxylic acid; hydrochloride salt

A solution of the compound from Example 1b) (1.6 g, 0.0062 mol.) in ethanol (75.0 mL), water (50.0 mL) and 3M aqu. sodium hydroxide (2.0 mL, 0.0062 mol.) was hydrogenated over 10% palladium on carbon (0.2 g) at room temperature and 50 psi for 2 h.

The reaction mixture was filtered, treated with 3M aqu. hydrochloric acid; (25.0 mL) then evaporated and the residue triturated with a little water to afford the title compound (1.18 g; 72%) as a brown solid. $^1$H NMR (300 MHz, $d_6$-DMSO) δ 10.90 (s, 1H), 10.5–8.5 (br s, 3H), 8.03 (d, J=8.2 Hz, 2H), 7.71 (d, J=8.2 Hz, 2H), 7.41 (d, J=8.2 Hz, 1H), 7.36 (d, J=1.6 Hz, 1H), 7.22 (dd, J=8.2, 1.6 Hz, 1H).

d) 1-(3,4-Dimethylphenyl)-3-methyl-3-pyrazolin-5-one

A solution of 3,4-dimethylphenylhydrazine hydrochloride (17.7 g; 0.1 mol.), ethyl acetoacetate (13.0 g; 0.1 mol.) and sodium acetate (8.2 g; 0.1 mol.) in glacial acetic acid; (250 mL) was stirred and heated under reflux for 24 h.

The mixture was cooled and evaporated and the residue dissolved in diethyl ether (1 L) and carefully washed with sat. aqu. sodium hydrogen carbonate (5×200 mL). The ethereal layer was evaporated to afford the title compound (15.4 g; 76%). $^1$H NMR (300 MHz, $d_6$-DMSO) δ 11.30 (br s, 1H), 7.49 (d, J=1.4 Hz, 1H), 7.43 (dd, J=8.2 Hz, 1H), 7.14 (d, J=8.2 Hz, 1H), 5.31 (s, 1H), 2.20 (s, 3H), 2.22 (s, 3H), 2.08 (s, 3H); MS(ES) m/z 203 [M+H].

e) 4'-{N'-[1-(3,4-Dimethylphenyl)-3-methyl-5-oxo-1,5-dihydropyrazol-4-ylidene]hydrazino}-3'-hydroxybiphenyl-4-carboxylic acid; hemihydrate A suspension of the compound from Example 1c) (1.0 g; 0.0044 mol.) in 1M aqu. hydrochloric acid; (15.0 mL) was cooled to 5° C. then treated dropwise with a solution of sodium nitrite (0.32 g; 0.0046 mol.) in water (5.0 mL). The yellow mixture was stirred at 5° C. for a further 10 min. then treated in one portion with the compound from Example 1d) (0.882 g, 0.0044 mol.) followed by the portion-wise addition of sodium hydrogen carbonate (1.8 g; 0.022 mol.) and ethanol (20.0 mL) ensuring the final pH of the reaction mixture is approximately 7–8. The red solution was then stirred at room temperature for 24 h.

The mixture was filtered to give a red solid which was slurried in water (50.0 mL) and then acidified with concentrated hydrochloric acid. Filtration afforded the title compound (0.68 g; 35%) as an orange powder, mp=280° C. (dec.). $^1$H NMR (300 MHz, $d_6$-DMSO) δ 13.62 (s, 1H), 13.2–12.2 (br s, 1H), 10.92 (s, 1H), 8.02 (d, J=8.2 Hz, 2H), 7.73–7.69 (m, 5H), 7.63 (d, 8.2 Hz, 1H), 7.31 (d, J=8.4 Hz, 1H), 7.29 (s, 1H), 71.9 (d, J=8.4 Hz, 1H), 2.30 (s, 3H), 2.26

(s, 3H), 2.2 (s, 3H); Anal. ($C_{25}H_{22}N_4O_4 \cdot 0.5H_2O$) calcd: C, 66.51; H, 5.13; N, 12.41. found: C, 66.74; H, 5.08; N, 12.36.

EXAMPLE 2

Preparation of 3'-{N'-[1-(3,4-dimethylphenyl)-3-methyl-5-oxo-1,5-dihydropyrazol-4-ylidene]hydrazino}-2'-hydroxybiphenyl-3-carboxylic acid a) 2-bromo-6-nitrophenol Following the procedure of Example 1a) except substituting 2-bromophenol for 3-bromophenol, the title compound was prepared (10.9 g; 25%) as a bright, yellow solid. $^1$H NMR (300 MHz, $CDCl_3$) δ 11.10 (S, 1 h), 8.13 (d, J=7.9 Hz, 1H), 7.89 (d, J=7.9 Hz, 1H), 6.90 (t, J=7.9 Hz, 1H).

b) 2-bromo-6-nitroanisole a mixture of the compound from Example 2a) (10.8 g; 0.0495 mol.), methyl iodide (3.4 mL; 0.00545 mol.) and potassium carbonate (8.2 g; 0.0592 mol.) in acetone (250 mL) was stirred and heated under reflux for 24 h.

The mixture was evaporated and the residue triturated with water to afford the title compound (8.7 g; 76%). mp 55–56° C. $^1$H NMR (300 MHz, $CDCl_3$ δ 7.81–7.74 (m, 2H), 7.13 (t, J=8.1 Hz, 1H), 4.02 (s, 3H); Anal. ($C_7H_6NO_3Br$) calcd: C, 36.24; H, 2.61; N, 6.04. found: C, 36.30; H, 2.59; N, 5.73.

c) 2'-methoxy-3'-nitrobiphenyl-3-carboxylic acid;

Following the procedure of Example 1b), except substituting the compound from Example 2b) for 5-bromo-2-nitrophenol and substituting 3-carboxyphenylboronic acid for 4-carboxyphenylboronic acid, the title compound was prepared (2.13 g; 47%) as a tan powder. $^1$H NMR (300 MHz, $d_6$-DMSO) δ 8.12 (s, 1H), 8.03 (d, J=7.9 Hz, 1H), 7.94 (dd, J=7.9 Hz, 1.5 Hz, 1H), 7.85 (d, J=7.9 Hz, 1H), 7.76 (dd, J=7.5, 1.5 Hz, 1H), 7.66 (t, J=7.5 Hz, 1H), 7.46 (t, j=7.9 Hz, 1H), 3.46 (s, 3H).

d) 2'-hydroxy-3'-nitrobiphenyl-3-carboxylic acid;

A solution of the compound from Example 2c) (2.13 g; 0.0077 mol.) in glacial acetic acid; (25.0 mL) and 48% aqu/hydrobromic acid; (25.0 mL) was stirred and heated under reflux for 5 h.

e) 3'-amino-2'-hydroxybiphenyl-3-carboxylic acid; hydrochloride salt

Following the procedure of Example 1c), except substituting the compound from Example 2d) for 3'-hydroxy-4'-nitrobiphenyl-4-carboxylic acid; the title compound was prepared (1.51 g; 100%) as a brown solid.11.3–8.7 (br s, 4H), 8.08 (s, 1H), 7.95 (d, J=7.8 Hz, 1H), 7.74 (d, J=7.8 Hz, 1H), 7.61 (t, J=7.8 Hz, 1H), 7.34 (dd, J=7.8, 1.4 Hz, 1H), 7.24 (dd, J=7.8, 1.3 Hz, 1H), 7.04 (t, J=7.8 Hz, 1H).

f) 3'-{N'-[1-(3,4-dimethylphenyl)-3-methyl-5-oxo-1,5-dihydropyrazol-4-ylidene]hydrazino}-2'-hydroxybiphenyl-3-carboxylic acid; hydrate Following the procedure of Example 1e), except substituting the compound from Example 2e) for 4'-amino-3'-hydroxybiphenyl-4-carboxylic acid; hydrochloride salt, the title compound was prepared (0.055 g; 32%) as an orange solid. mp 228° C. (dec.). $^1$H NMR (300 MHz, $d_6$-DMSO) δ 13.76 (s, 1H), 13.12 (s, 1H), 9.70 (s, 1H), 8.14 (s, 1H), 7.97 (dd, J=7.7 Hz, 1H), 7.81 (dd, J=7.7 Hz, 1H), 7.74–7.60 (m, 5H), 7.22–7.13 (m, 3H), 2.34 (s, 3H), 2.27 (s, 3H), 2.23 (s, 3H); Anal. ($C_{25}H_{22}N_4O_4 \cdot 1.0H_2O$) calcd: C, 65.21; H, 5.25; N, 12.17. found: C, 65.60; H, 4.96; N, 12.04.

EXAMPLE 3

Capsule Composition

An oral dosage form for administering a presently invented agonist of the TPO receptor is produced by filing a standard two piece hard gelatin capsule with the ingredients in the proportions shown in Table I, below.

TABLE I

| INGREDIENTS | AMOUNTS |
|---|---|
| 4'-{N'-[1-(3,4-Dimethylphenyl)-3-methyl-5-oxo-1,5-dihydropyrazol-4-ylidene]hydrazino}-3'-hydroxybiphenyl-4-carboxylic acid; (Compound of Example 1) | 25 mg |
| Lactose | 55 mg |
| Talc | 16 mg |
| Magnesium Stearate | 4 mg |

EXAMPLE 4

Injectable Parenteral Composition

An injectable form for administering a presently invented agonist of the TPO receptor is produced by stirring 1.5% by weight of 4'-{N'-[1-(3,4-dimethylphenyl)-3-methyl-5-oxo-1,5-dihydropyrazol-4-ylidene]hydrazino}-3'-hydroxybiphenyl-3-carboxylic acid; in 10% by volume propylene glycol in water.

EXAMPLE 5

Tablet Composition

The sucrose, calcium sulfate dihydrate and a presently invented agonist of the TPO receptor, as shown in Table II below, are mixed and granulated in the proportions shown with a 10% gelatin solution. The wet granules are screened, dried, mixed with the starch, talc and stearic acid;, screened and compressed into a tablet.

TABLE II

| INGREDIENTS | AMOUNTS |
|---|---|
| 3'-{N'-[1-(3,4-dimethylphenyl)-3-methyl-5-oxo-1,5-dihydropyrazol-4-ylidene]hydrazino}-2'-hydroxybiphenyl-3-carboxylic acid; (Compound of Example 2) | 20 mg |
| calcium sulfate dihydrate | 30 mg |
| sucrose | 4 mg |
| starch | 2 mg |
| talc | 1 mg |
| stearic acid | 0.5 mg |

Preferred among the compounds of the present invention are the following;
3'-{N'-[3-cyclopropyl-1-(3,4-dimethylphenyl)-5-oxo-1,5-dihydropyrazol-4-ylidene]hydrazino}-2'-hydroxybiphenyl-3-carboxylic acid;
[1-(4-fluoro-3-methylphenyl)-3-methyl-5-oxo-1,5-dihydropyrazol-4-ylidene]hydrazino}-2'-hydroxybiphenyl-3-carboxylic acid;
3'-{N'-[3-methyl-5-oxo-1-(4-trifluoromethylphenyl)-1,5-dihydropyrazol-4-ylidene]hydrazino}-2'-hydroxybiphenyl-3-carboxylic acid;
3'-{N'-[1-(3,4-Dimethylphenyl)-3-methyl-5-oxo-1,5-dihydropyrazol-4-ylidene]hydrazino}-2'-hydroxybiphenyl-3-carboxylic acid;

3-{N'-[1-(3,4-dimethylphenyl)-3-methyl-5-oxo-1,5-dihydropyrazol-4-ylidene]hydrazino}-2-hydroxy-3'-tetrazol-5-ylbiphenyl;

3'-{N'-[1-(3-fluoro-4-methylphenyl)-3-methyl-5-oxo-1,5-dihydropyrazol-4-ylidene]hydrazino}-2'-hydroxybiphenyl-3-carboxylic acid;

3'-{N'-[1-(3,4-dimethylphenyl)-3-ethyl-5-oxo-1,5-dihydropyrazol-4-ylidene]hydrazino}-2'-hydroxybiphenyl-3-carboxylic acid;

3-{N'-[1-(3,4-dimethylphenyl)-3-ethyl-5-oxo-1,5-dihydropyrazol-4-ylidene]hydrazino}-2-hydroxy-3'-tetrazol-5-ylbiphenyl;

3'-{N'-[1-(3-chloro-4-methylphenyl)-3-methyl-5-oxo-1,5-dihydropyrazol-4-ylidene]hydrazino}-2'-hydroxybiphenyl-3-carboxylic acid;

3'-{N'-[1-(3,4-dimethylphenyl)-3-methyl-5-oxo-1,5-dihydropyrazol-4-ylidene]hydrazino}-5'-fluoro-2'-hydroxybiphenyl-3-carboxylic acid;

3'-{N'-[1-(3,4-Dimethylphenyl)-3-methoxy-5-oxo-1,5-dihydropyrazol-4-ylidene]hydrazino}-2'-hydroxybiphenyl-3-carboxylic acid;

3-Aza-3'-{N'-[1-(4-tert-butylphenyl)-3-methyl-5-oxo-1,5-dihydropyrazol-4-ylidene]hydrazino}-2'-hydroxybiphenyl-5-carboxylic acid;

3'-{N'-[3-methyl-1-(4-methylphenyl)-5-oxo-1,5-dihydropyrazol-4-ylidene]hydrazino}-2'-hydroxybiphenyl-3-carboxylic acid;

[1-(4-fluoro-3-methylphenyl)-3-methyl-5-oxo-1,5-dihydropyrazol-4-ylidene]hydrazino}-2'-hydroxybiphenyl-3-carboxylic acid;

3'-{N'-[1-(3,5-dimethylphenyl)-3-methyl-5-oxo-1,5-dihydropyrazol-4-ylidene]hydrazino}-2'-hydroxybiphenyl-3-carboxylic acid;

(3-{N'-[1-(3,4-dimethylphenyl)-3-methyl-5-oxo-1,5-dihydropyrazol-4-ylidene]hydrazino}-2-hydroxy-3'-biphenyl)-1,1,1,-trifluoromethanesulfonamide; and 3'-{N'-[1-(3,4-dimethylphenyl)-5-oxo-1,5-dihydropyrazol-4-ylidene]hydrazino}-2'-hydroxybiphenyl-3-carboxylic acid.

Particularly preferred among the compounds of the invention are following;

3'-{N'-[3-cyclopropyl-1-(3,4-dimethylphenyl)-5-oxo-1,5-dihydropyrazol-4-ylidene]hydrazino}-2'-hydroxybiphenyl-3-carboxylic acid;

[1-(4-fluoro-3-methylphenyl)-3-methyl-5-oxo-1,5-dihydropyrazol-4-ylidene]hydrazino}-2'-hydroxybiphenyl-3-carboxylic acid;

3'-{N'-[3-methyl-5-oxo-1-(4-trifluoromethylphenyl)-1,5-dihydropyrazol-4-ylidene]hydrazino}-2'-hydroxybiphenyl-3-carboxylic acid;

3'-{N'-[1-(3,4-Dimethylphenyl)-3-methyl-5-oxo-1,5-dihydropyrazol-4-ylidene]hydrazino}-2'-hydroxybiphenyl-3-carboxylic acid;

3-{N'-[1-(3,4-dimethylphenyl)-3-methyl-5-oxo-1,5-dihydropyrazol-4-ylidene]hydrazino}-2-hydroxy-3'-tetrazol-5-ylbiphenyl;

3'-{N'-[1-(3-fluoro-4-methylphenyl)-3-methyl-5-oxo-1,5-dihydropyrazol-4-ylidene]hydrazino}-2'-hydroxybiphenyl-3-carboxylic acid;

3'-{N'-[1-(3,4-dimethylphenyl)-3-ethyl-5-oxo-1,5-dihydropyrazol-4-ylidene]hydrazino}-2'-hydroxybiphenyl-3-carboxylic acid;

3-{N'-[1-(3,4-dimethylphenyl)-3-ethyl-5-oxo-1,5-dihydropyrazol-4-ylidene]hydrazino}-2-hydroxy-3'-tetrazol-5-ylbiphenyl;

3'-{N'-[1-(3-chloro-4-methylphenyl)-3-methyl-5-oxo-1,5-dihydropyrazol-4-ylidene]hydrazino}-2'-hydroxybiphenyl-3-carboxylic acid;

3'-{N'-(1-(3,4-dimethylphenyl)-3-methyl-5-oxo-1,5-dihydropyrazol-4-ylidene]hydrazino}-5'-fluoro-2'-hydroxybiphenyl-3-carboxylic acid;

3'-{N'-[1-(3,4-Dimethylphenyl)-3-methoxy-5-oxo-1,5-dihydropyrazol-4-ylidene]hydrazino}-2'-hydroxybiphenyl-3-carboxylic acid;

3-Aza-3'-{N'-[1-(4-tert-butylphenyl)-3-methyl-5-oxo-1,5-dihydropyrazol-4-ylidene]hydrazino}-2'-hydroxybiphenyl-5-carboxylic acid; and 3'-{N'-[3-methyl-1-(4-methylphenyl)-5-oxo-1,5-dihydropyrazol-4-ylidene]hydrazino}-2'-hydroxybiphenyl-3-carboxylic acid.

Particularly preferred among the compounds of the invention are following;

3'-{N'-[3-cyclopropyl-1-(3,4-dimethylphenyl)-5-oxo-1,5-dihydropyrazol-4-ylidene]hydrazino}-2'-hydroxybiphenyl-3-carboxylic acid;

[1-(4-fluoro-3-methylphenyl)-3-methyl-5-oxo-1,5-dihydropyrazol-4-ylidene]hydrazino}-2'-hydroxybiphenyl-3-carboxylic acid;

3'-{N'-[3-methyl-5-oxo-1-(4-trifluoromethylphenyl)-1,5-dihydropyrazol-4-ylidene]hydrazino}-2'-hydroxybiphenyl-3-carboxylic acid;

3-{N'-[1-(3,4-dimethylphenyl)-3-methyl-5-oxo-1,5-dihydropyrazol-4-ylidene]hydrazino}-2-hydroxy-3'-tetrazol-5-ylbiphenyl;

3'-{N'-1-(3,4-Dimethylphenyl)-3-methyl-5-oxo-1,5-dihydropyrazol-4-ylidene]hydrazino}-2'-hydroxybiphenyl-3-carboxylic acid;

3'-{N'-[1-(3-fluoro-4-methylphenyl)-3-methyl-5-oxo-1,5-dihydropyrazol-4-ylidene]hydrazino}-2'-hydroxybiphenyl-3-carboxylic acid;

3'-{N'-[1-(3,4-dimethylphenyl)-3-ethyl-5-oxo-1,5-dihydropyrazol-4-ylidene]hydrazino}-2'-hydroxybiphenyl-3-carboxylic acid; and 3-{N'-[1-(3,4-dimethylphenyl)-3-ethyl-5-oxo-1,5-dihydropyrazol-4-ylidene]hydrazino}-2-hydroxy-3'-tetrazol-5-ylbiphenyl.

The most preferred among the compounds of the invention is,

3'-{N'[1-(3,4-Dimethylphenyl)-3-methyl-5-oxo-1,5-dihydropyrazol-4-ylidene]hydrazino}-2'-hydroxybiphenyl-3-carboxylic acid.

The compound 3'-{N'[1-(3,4-Dimethylphenyl)-3-methyl-5-oxo-1,5-dihydropyrazol-4-ylidene]hydrazino}-2'-hydroxybiphenyl-3-carboxylic acid demonstrated an activity of, $EC_{50}=0.03$ uM, 100% TPO in the above proliferation assay.

While the preferred embodiments of the invention are illustrated by the above, it is to be understood that the invention is not limited to the precise instructions herein disclosed and that the right to all modifications coming within the scope of the following claims is reserved.

What is claimed is:

1. A compound selected from the group consisting essentially of:

3'-{N'-[1-(3,4-Dimethylphenyl)-3-methyl-5-oxo-1,5-dihydropyrazol-4-ylidene]hydrazino}-2'-hydroxybiphenyl-3-carboxylic acid, and a pharmaceutically acceptable salt, a hydrate, a solvate, and an ester, thereof.

2. The compound of claim 1, wherein the compound is the pharmaceutically acceptable salt.

3. The pharmaceutical composition which comprises the compound of claim 1 and a pharmaceutically acceptable carrier.

4. The compound of claim 1, wherein the compound is 3'-{N'-[1-(3,4-Dimethylphenyl)-3-methyl-5-oxo-1,5-dihydropyrazol-4-ylidene]hydrazino}-2'-hydroxybiphenyl-3-carboxylic acid.

5. A method of treating thrombocytopenia in a human in need thereof which comprises administering to such human a therapeutically effective amount of the compound of claim 1.

6. The method of claim 5 wherein the compound is administered orally.

7. The method of claim 5 wherein the compound is administered parenterally.

8. The method of claim 5 further comprising co-administering a therapeutically effective amount of an agent selected from the group consisting of: a colony stimulating factor, cytokine, chemokine, interleukin or cytokine receptor agonist or antagonist, soluble receptor, receptor agonist or antagonist antibody, and small molecule or peptide that acts by the same mechanisms as one or more of said agents.

9. The method of claim 8 wherein the agent is selected from the group consisting of: G-CSF, GM-CSF, TPO, M-CSF, EPO, Gro-beta, IL-11, SCF, FLT3 ligand, LIF, IL-3, IL-6, IL-1, Progenipoietin, NESP, SD-01, IL-8, IL-5, and a biologically active derivative of any of said agents.

10. The method of claim 5 wherein said thrombocytopenia is due to myelosuppression caused by chemotherapy or radiation therapy.

11. The method of claim 5 wherein said thrombocytopenia is due to an organ transplant.

12. The method of claim 5 wherein said thrombocytopenia is due to bone marrow, stem cell, or liver transplant.

13. The method of claim 5 wherein said thrombocytopenia is due to idiopathic thrombocytopenia purpura (ITP).

14. The method of claim 5 wherein said thrombocytopenia is due to myelodysplastic syndromes (MDS), aplastic anemia or leukemia.

15. The method of claim 5 wherein said thrombocytopenia is due to viral, fungal, microbial or parasitic infection.

16. The method of claim 5 wherein said thrombocytopenia is due to liver dysfunction.

17. The method of claim 5 wherein said thrombocytopenia is due to surgical procedures.

18. The method of claim 5 wherein said thrombocytopenia is due to treatment with antiviral or antibiotic agents.

19. A process for preparing a pharmaceutical composition containing a pharmaceutically acceptable carrier or diluent and an effective amount of the compound of claim 1, which process comprises bringing said compound into association with the pharmaceutically acceptable carrier or diluent.

20. The pharmaceutical composition of claim 3 further comprising a therapeutically effective amount of an agent selected from the group consisting of: a colony stimulating factor, cytokine, chemokine, interleukin, and cytokine receptor agonist.

21. The pharmaceutical composition of claim 20 wherein the agent is selected from the group consisting of: G-CSF, GM-CSF, TPO, M-CSF, EPO, Gro-beta, IL-11, SCF, FLT3 Ligand, LIF, IL-3, IL-6, IL-1, IL-5, and a biologically active derivative of any of said agents.

22. A compound selected from the group consisting essentially of:
4'-{N'-[1-(3,4-Dimethylphenyl)-3-methyl-5-oxo-1,5-dihydropyrazol-4-ylidene]hydrazino}-3'-hydroxybiphenyl-4-carboxylic acid, and a pharmaceutically acceptable salt, a hydrate, a solvate, and an ester, thereof.

* * * * *

UNITED STATES PATENT AND TRADEMARK OFFICE
CERTIFICATE OF CORRECTION

PATENT NO. : 7,160,870 B2
APPLICATION NO. : 10/296688
DATED : January 9, 2007
INVENTOR(S) : Duffy et al.

It is certified that error appears in the above-identified patent and that said Letters Patent is hereby corrected as shown below:

Title page, between Items 65 and 51, add the following section,

Related U.S. Application Data
(60)  Provisional application No. 60/207,084, filed on May 25, 2000, provisional application No. 60/228,929, filed on August 30, 2000.

Column 1,
Line 38, "megaklaryocytopoiesis" should be -- megakaryocytopoiesis --

Column 3,
Line 47, "—S(O)"R$^4$" should be -- —S(O)$_n$R$^4$ --

Column 5,
Line 7, "—S(O)"R$^4$" should be -- —S(O)$_n$R$^4$ --

Column 8,
Line 40, "Buthylphenyl" should be -- Butylphenyl --

Column 9,
Line 54, "2-hydroxybiphenyl" should be -- 2'-hydroxybiphenyl --

Column 10,
Line 50, "3-etboxy" should be -- 3-ethoxy --

Column 11,
Line 29, "2-hydroxybiphenyl" should be -- 2'-hydroxybiphenyl --

Column 12,
Line 10, "sulfonarnide" should be -- sulfonamide --

Column 16,
Line 59, "dimethylformnamide" should be -- dimethylformamide --

UNITED STATES PATENT AND TRADEMARK OFFICE
CERTIFICATE OF CORRECTION

| | |
|---|---|
| PATENT NO. | : 7,160,870 B2 |
| APPLICATION NO. | : 10/296688 |
| DATED | : January 9, 2007 |
| INVENTOR(S) | : Duffy et al. |

It is certified that error appears in the above-identified patent and that said Letters Patent is hereby corrected as shown below:

<u>Column 18,</u>
Line 51, "(i)" should be -- (I) --

Signed and Sealed this

Nineteenth Day of June, 2007

JON W. DUDAS
*Director of the United States Patent and Trademark Office*

UNITED STATES PATENT AND TRADEMARK OFFICE
CERTIFICATE OF CORRECTION

PATENT NO. : 7,160,870 B2  
APPLICATION NO. : 10/296688  
DATED : January 9, 2007  
INVENTOR(S) : Duffy et al.

Page 1 of 1

It is certified that error appears in the above-identified patent and that said Letters Patent is hereby corrected as shown below:

Column 20,
Line 26, "Scheme II" should be -- Scheme III --

Column 22,
Line 55, "2'-[methoxybiphenyl" should be -- 2'-methoxybiphenyl --

Column 25,
Line 41: "MT7TPO" should be -- UT7TPO --

Column 26,
Line 6, "preparation" should be -- preparations --

Column 28,
Line 5, "tetrallistriphyenylphosphino" should be -- tetrakistriphenylphosphino --
Line 67, "71.9" should be -- 7.19 --

Column 29,
Line 44, after line 44 add the following paragraph:

--       The mixture was cooled and filtered to afford the title compound (1.57 g; 79%) as a tan powder. $^1$H NMR (300 MHz, $d_6$-DMSO) δ 13.90 (s, 1H), 10.66 (s, 1H), 8.12 (t, J = 1.7 Hz, 1H), 8.07 (dd, J = 8.4, 1.7 Hz, 1H), 7.98 (dt, 7.8, 1.5 Hz, 1H), 7.79 (dt, J = 8.1, 1.7 Hz, 1H), 7.74 (dd, J = 7.5, 1.7 Hz, 1H), 7.62 (t, J = 7.8 Hz, 1H), 7.17 (dd, J = 8.4, 7.5 Hz, 1H). --

Signed and Sealed this

Twenty-first Day of October, 2008

JON W. DUDAS  
*Director of the United States Patent and Trademark Office*